US008585927B2

(12) United States Patent
Ando et al.

(10) Patent No.: US 8,585,927 B2
(45) Date of Patent: *Nov. 19, 2013

(54) SEMICONDUCTOR-NANOPARTICLE-DISPERSED SMALL GLASS PARTICLES AND PROCESS FOR PREPARING THE SAME

(75) Inventors: Masanori Ando, Ikeda (JP); Norio Murase, Ikeda (JP); Chunliang Li, Ikeda (JP); Ping Yang, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 1409 days.

This patent is subject to a terminal disclaimer.

(21) Appl. No.: 11/992,403

(22) PCT Filed: Sep. 21, 2006

(86) PCT No.: PCT/JP2006/318748
§ 371 (c)(1),
(2), (4) Date: Mar. 21, 2008

(87) PCT Pub. No.: WO2007/034877
PCT Pub. Date: Mar. 29, 2007

(65) Prior Publication Data
US 2009/0108235 A1    Apr. 30, 2009

(30) Foreign Application Priority Data

Sep. 22, 2005 (JP) ................................. 2005-275012
Jan. 6, 2006 (JP) ..................................... 2006-1040
Feb. 17, 2006 (JP) .................................. 2006-41642
Mar. 20, 2006 (JP) .................................. 2006-77334

(51) Int. Cl.
*C09K 11/08* (2006.01)

(52) U.S. Cl.
USPC .................................................. 252/301.4 F

(58) Field of Classification Search
USPC ........ 252/301.4 R, 301.6 R, 301.6 S, 301.4 F, 252/301.6 F, 301.4 S, 301.16, 301.36; 428/690; 313/467, 468
See application file for complete search history.

(56) References Cited

U.S. PATENT DOCUMENTS 6,444,143 B2 *   9/2002   Bawendi et al. ......... 252/301.6 S
6,592,945 B2 *   7/2003   Suzuki et al. ................. 427/387

(Continued)

FOREIGN PATENT DOCUMENTS

JP   2002-211935     7/2002
JP   2003-321226    11/2003

(Continued)

OTHER PUBLICATIONS

Yang et al., Water-soluble silica-overcoated Cds:Mn/Snz semiconductor quantum dots, Oct. 2004, vol. 121, Issue 15, pp. 7421-7426.*

(Continued)

*Primary Examiner* — Emily Le
*Assistant Examiner* — Lynne Edmondson
(74) *Attorney, Agent, or Firm* — Kratz, Quintos & Hanson, LLP

(57) ABSTRACT

The present invention provides semiconductor-nanoparticle-dispersed small silica glass particles that emit bright fluorescent light with high fluorescence quantum yield and high density, compared to the conventional semiconductor-nanoparticle-dispersed small glass particles, and that have excellent fluorescence intensity stability over time; and a process for preparing the same. The semiconductor-nanoparticle-dispersed silica glass particles have a mean particle size of not less than 10 nanometers and not more than 5 micrometers, and contain a hydrolyzed alkoxide and semiconductor nanoparticles at a concentration of not less than $2 \times 10^{-5}$ mol/l and not more than $1 \times 10^{-2}$ mol/l. The particles emit fluorescent light with a fluorescence quantum yield (quantum yield) of 25% or more (and 60% or more), when dispersed in a solution.

12 Claims, 6 Drawing Sheets

(56) References Cited

U.S. PATENT DOCUMENTS

| | | | |
|---|---|---|---|
| 7,326,365 B2* | 2/2008 | Bawendi et al. | 252/301.4 R |
| 7,824,767 B2* | 11/2010 | Murase et al. | 428/333 |
| 2006/0029802 A1* | 2/2006 | Ying et al. | 428/403 |
| 2006/0054863 A1* | 3/2006 | Dai et al. | 252/301.4 R |
| 2006/0097624 A1* | 5/2006 | Murase et al. | 313/503 |

FOREIGN PATENT DOCUMENTS

| | | | |
|---|---|---|---|
| JP | 2005-189237 | | 7/2005 |
| JP | 2005-281019 | | 10/2005 |
| JP | 2005281019 A | * | 10/2005 |
| WO | WO 2004/000971 A1 | | 12/2003 |

OTHER PUBLICATIONS

Yang et al., Water-soluble silica-overcoated Cds:Mn/ZnS semiconductor quantum dots, Oct. 2004, vol. 121, Issue 15, pp. 7421-7426.*

JP2005-281019 A translation (text starts on p. 4).*

Nann et al, 'Single Quantum Dots in Spherical Silica Particles', Oct. 2004, Angew.Chem. Int. Ed., vol. 43, Issue 18, pp. 5393-5396.*

Selvan et al., "Formation of Luminescent CdTe-Silica Noanoparticles through an Inverse Microemulsion Technique"; Chemistry Letters vol. 33, No. 4; 434-435, 2004.

Selvan et al., "Robust, Non-Cytotoxic, Silica-Coated CdSe Quantum Dots with Efficient Photoluminescence"; Advanced Materials vol. 17, 1620-1625, 2005.

Yang et al., "Preparation of Fluorescent SiO2 Particles with Single CdTe Nanocrystal Cores by the Reverse Microemulsion Method"; Advanced Materials vol. 17, 2354-2357, 2005.

Yi et al., "Silica-Coated Nanocomposites of Magnetic Nanoparticles and Quantum Dots"; Journal of American chemical Society vol. 127, 4990-4991, 2005.

Darbandi et al., "Single Quantum Dots in Silica Spheres by Microemulsion Synthesis"; Chemistry of Materials vol. 17, 5720-5725, 2005.

Chan et al., "Incorporation of Luminescent Nanocrystals into Monodisperse Core-Shell Silica Microspheres"; Advanced Materials vol. 16, 2092-2097, 2004.

Gerion et al., "Synthesis and Properties of Biocompatible Water-Soluble Silica-coated CdSe/ZnS Semiconductor Quantum Dots"; Journal of Physical Chemistry, vol. 105, 8861-8871, 2001.

Nann et al., "Single Quantum Dots in Spherical Silica Particles"; Angewandte Chemie International Edition, vol. 43, 5393-5396, 2004.

Rogach, Audrey L., et al., "'Raisin Bun'—Type Composite Spheres of Silica and Semiconductor Nanocrystals," Chem. Mater. 2000, No, 12, pp. 2676-2685.

\* cited by examiner

SEMICONDUCTOR-NANOPARTICLE-DISPERSED SMALL GLASS PARTICLES AND PROCESS FOR PREPARING THE SAME

TECHNICAL FIELD

The present invention relates to small glass particles with dispersed semiconductor nanoparticles. The present invention particularly relates to small glass particles containing fluorescent light (photoluminescence)-emitting semiconductor nanoparticles dispersed therein, and a process for preparing the same.

BACKGROUND ART

In recent years, the need has increased for a high-performance, energy-saving color display that has high brightness, high resolution and low power consumption. The key to developing such a display is a high-performance fluorescent material that emits light of various colors, such as the three primary colors red, green and blue (RGB), with high brightness and fluorescence quantum yield. Such a high-performance fluorescent material is also essential in new energy-saving solid state lighting systems, the demand for which is increasing.

Fluorescent materials using rare earth ions and/or transition metal ions have been used for displays, etc. because of their excellent durability compared to organic dyes, etc. However, such fluorescent materials are not always satisfactory in terms of brightness and color-rendering properties. Therefore, there is a desire for fluorescent materials that have higher brightness levels than those of known fluorescent materials.

Semiconductor nanoparticles that can emit bright fluorescent light of various wavelengths according to particle size, even under UV radiation of the same wavelength, have been attracting attention as highly potential candidates for such a new high-performance fluorescent material. Fluorescent materials find application not only in displays and lighting systems but also as fluorescent probes that are produced by bonding such fluorescent materials to biomolecules. Even in such an application field, semiconductor nanoparticles whose fluorescence intensity reduction with time is small, compared to that of the organic dyes used so far, are attracting attention.

Semiconductors used as such fluorescent materials are mainly II-VI semiconductors (e.g., cadmium sulfide (CdS), zinc selenide (ZnSe), cadmium selenide (CdSe), zinc telluride (ZnTe), cadmium telluride (CdTe), etc.). Such semiconductors are direct-transition-type semiconductors and have an emission lifetime of about 10 nanoseconds. This emission lifetime is about 5 orders of magnitude shorter than known fluorescent materials using rare earth ions and/or transition metal ions whose transitions are mainly forbidden transitions. Therefore, such II-VI semiconductors can repeat the absorption of excitation light and emission of fluorescent light remarkably quickly, and fluorescent light of much higher brightness can be obtained. The short emission lifetime means a quick response to the ON and OFF of excitation light. Moreover, the deterioration of the semiconductor nanoparticles is much less than that of organic dyes.

Methods for producing such semiconductor nanoparticles in aqueous solutions and those in non-aqueous solutions have been developed. However, the semiconductor nanoparticles produced in a solution gradually aggregate, which starts immediately after the production, thus resulting in the deterioration of light emission characteristics. The nanoparticles produced in a non-aqueous solution have particularly poor resistance to water, and the fluorescence is rapidly reduced in the presence of even a trace amount of water. Another problem is that nanoparticle solutions, as is, are not suitable for technological applications. Therefore, it is necessary to incorporate, i.e., to disperse and fix semiconductor nanoparticles in a matrix such as transparent glass or the like, thus producing a solid-state material that maintains high-brightness light emission characteristics in various environments for a long period of time, and is suitable for technological application.

Examples of solid matrices in which nanoparticles are retained include glass and transparent organic polymer materials. Glass has the following advantages and is thus excellent: compared to organic polymers, glass has high transparency, high UV resistance, and low permeability to water and oxygen, and can therefore prevent the deterioration of nanoparticles dispersed in the matrix due to chemical changes for a long period of time. Using a sol-gel process to produce a glass is advantageous. When using a sol-gel process, a glass is formed under mild conditions, i.e., at room temperature and under normal pressure. Therefore, the semiconductor nanoparticles are dispersed and fixed in a transparent glass, while the particle size and high fluorescence quantum yield achieved immediately after the production thereof by an aqueous solution method are maintained. Once a solid glass incorporating nanoparticles is formed, the aggregation of nanoparticles and degradation by oxidation are less likely to progress, and a material that can stably emit high-brightness fluorescent light for a long period of time can be provided.

Examples of fluorescent glass produced by dispersing and fixing semiconductor nanoparticles in a glass using a sol-gel process include bulky glass, small glass particles, and thin glass films, and several production methods thereof have been attempted. Among these, small glass particles dispersed semiconductor nanoparticles therein are important as a powdery fluorescent material that is deposited on a substrate to produce a light-emitting device, such as a display or a lighting system, and as a fluorescent probe that is produced by bonding such small glass particles to biomolecules. The description below is limited to fluorescent small glass particles produced by dispersing and fixing semiconductor nanoparticles in a glass using a sol-gel process.

There are several known fluorescent small glass particles produced by dispersing and fixing semiconductor nanoparticles therein using a sol-gel process, and production methods thereof, as described below.

The first known small glass particles incorporating semiconductor nanoparticles are fluorescent small glass particles produced by dispersing and fixing semiconductor nanoparticles in a glass using a sol-gel process, and the fluorescence quantum yield thereof is about 1 to about 20%. The first production method thereof comprises: forming reverse micelles of a surfactant in a hydrophobic organic solvent; then adding an nanoparticle-dispersed aqueous solution to the reverse micelle solution to form reverse micelles containing the nanoparticle-dispersed aqueous solution therein; and adding to the reaction solution an alkoxide such as tetraethoxysilane (TEOS) as a reactant for glass formation to allow a sol-gel reaction to proceed in the reverse micelles, thus providing a small glass particle containing nanoparticles dispersed and fixed therein (Patent Document 1 to Non-Patent Documents 1 to 5).

The first production method was expected to prevent the aggregation of nanoparticles in the glass formation process by a sol-gel reaction, because the nanoparticles are separately present in the respective reverse micelles. This method was actually able to produce small glass particles containing nanoparticles dispersed and fixed therein.

However, the fluorescence quantum yield of nanoparticle-dispersed small glass particles obtained by the first production method is 5 to 10% in Patent Document 1 and Non-Patent Document 1; 14 to 20% in Non-Patent Document 2; 7% in Non-Patent Document 3; and 1 to 11% in Non-Patent Document 4. In any case, the fluorescence quantum yield is as low as 20% or less, and unsatisfactory for practical use.

Among the first production methods, those disclosed in Patent Document 1 and Non-Patent Document 1 produce small glass particles comprising semiconductor nanoparticles fixed near the outer surfaces of the glass particles, not inside the glass particles. When semiconductor nanoparticles are fixed near the outer surfaces of the glass particles, shielding of the semiconductor nanoparticle from the external atmosphere is insufficient, compared to semiconductor nanoparticles fixed inside the glass. Therefore, long-term stability of fluorescence characteristics tends to be insufficient. One reason considered as to why the semiconductor nanoparticles tend to be present near the outer surface of the glass particle is as follows: in the sol-gel reaction, alkoxide is hydrolyzed to form a silica network structure. When the hydrolysis of alkoxide is allowed to proceed, a mixture of an unreacted alkoxide having a low viscosity and semiconductor nanoparticles gradually changes to a mixture of a highly viscous gel and semiconductor nanoparticles. During that process, semiconductor nanoparticles are easily expelled from the silica network structure. As a result, after the sol-gel reaction has been completed to form a glass, the semiconductor nanoparticles are fixed near the outer surface of the formed glass particle, rather than inside the glass particle.

Bawendi, et al. (Non-Patent Document 6) describes fluorescent small glass particles containing semiconductor nanoparticles dispersed and fixed therein, and a production method thereof, referred to herein as a second production method. The second production method comprises: preparing nanoparticles in an organic solvent beforehand; dispersing the thus obtained nanoparticles into a solution containing an amino-group containing alcohol and a silane coupling agent to substitute organic molecules, such as thioglycolic acid, formed as a coating on the surface of nanoparticles in the nanoparticle preparation process with the amino group-containing alcohol and silane coupling agent; then adding the nanoparticle dispersion to a dispersion of nanoparticle-free small silica glass particles and an organic polymer in an alcohol; and then adding aqueous ammonia and alkoxide to allow a sol-gel reaction to proceed.

This method produces a fluorescent small glass particle comprising a nanoparticle-free small glass particle whose surface is coated with a nanoparticle-containing sol-gel glass layer. However, because the nanoparticles are present only near the surface layer of the glass particle and the core of the glass particle does not contain nanoparticles, it is impossible to increase the concentration of nanoparticles dispersed in the glass particle, and it is thus difficult to obtain strong luminescence and high fluorescence quantum yield.

Non-Patent Documents 7 and 8 describe a method of producing semiconductor-nanoparticle-containing small glass particles comprising: preparing semiconductor nanoparticles coated with a surfactant; chemically modifying the semiconductor nanoparticles with a silane coupling agent, alkoxide, or the like; and then hydrolyzing the silane coupling agent, alkoxide or the like, which is referred to herein as a third production method. However, this method has the following disadvantage for practical use. Because only one semiconductor nanoparticle can be contained in one small glass particle, the concentration of nanoparticles in the glass particles is very low, and it is difficult to obtain bright fluorescence.

Patent Document 1: Japanese Unexamined Patent Publication No. 2002-211935,
Non-Patent Document 1: Selvan, Li, Ando, Murase, Chemistry Letters, vol. 33, No. 4, page 434 (2004),
Non-Patent Document 2: Selvan, Tan, Ying, Advanced Materials, vol. 17, page 1620 (2005),
Non-Patent Document 3: Yang, Gao, Advanced Materials, vol. 17, page 2354 (2005),
Non-Patent Document 4: Yi, Selvan, Lee, Papaefthymiou, Kundaliya, Ying, Journal of American Chemical Society, vol. 127, page 4990 (2005),
Non-Patent Document 5: Darbandi, Thomann, Nann, Chemistry of Materials, vol. 17, page 5720 (2005),
Non-Patent Document 6: Chan, Zimmer, Stroh, Steckel, Jain, Bawendi, Advanced Materials, vol. 16, page 2092 (2004),
Non-Patent Document 7: Gerion, Pinaud, Williams, Parak, Zanchet, Weiss, Alivisatos, Journal of Physical Chemistry B, vol. 105, page 8861 (2001),
Non-Patent Document 8: Nann, Mulvaney, Angewandte Chemie International Edition, vol. 43, page 5393 (2004).

DISCLOSURE OF THE INVENTION

Problems to be Solved by the Invention

An object of the present invention is to provide semiconductor-nanoparticle-dispersed small silica glass particles that emit bright fluorescent light of visible wavelength with high fluorescence quantum yield and high concentration of nanoparticles, compared to known semiconductor-nanoparticle-dispersed small glass particles, and have excellent fluorescence intensity stability over time, and a process for preparing the same. The silica glass herein means a material containing a Si—O—Si bond in at least a portion thereof.

Means for Solving the Problem

The present inventors attributed the low fluorescence quantum yield, i.e., about 20% at most, of known semiconductor nanoparticle-dispersed small glass particles to the production methods and structures thereof.

More specifically, the inventors considered as follows. Because the first known production method uses a mixture of unreacted alkoxide and semiconductor nanoparticles as the starting material, it is necessary to stir the reaction solution for about 1 to about 3 days to allow the sol-gel reaction to fully proceed to form small glass particles. The nanoparticles in the solution gradually deteriorate during such long-term stirring, which results in reduced fluorescence intensity.

The inventors further considered the following. Because unreacted alkoxide in the early stage of the reaction has a viscosity lower than hydrolyzed alkoxide, semiconductor nanoparticles are easily removed from the silica network structure when the structure is being developed in the sol-gel reaction process. As a result, after the sol-gel reaction has been completed to form a glass, semiconductor nanoparticles tend to be present and fixed near the outer surface of the small glass particles, not inside of the formed small glass particles, thus reducing the fluorescence quantum yield due to the aggregation of semiconductor nanoparticles and reducing the fluorescence intensity with time due to the ease of contact with the external atmosphere because of the thin glass coating layer.

Another possibility the inventors considered was that due to the ionic surfactant used, electrostatic repulsion occurs between the electric charge that is present in reverse micelles formed in the solution and the electric charge of another surfactant used to coat the nanoparticle surface. As a result, nanoparticles are not incorporated in a high concentration into the reverse micelles, thus resulting in a low fluorescence intensity of the obtained glass particle.

In the second known production method, nanoparticles are present only near the surface layer of a glass particle and are not contained in the core of the glass particle, as described above. Therefore, it is difficult to enhance the concentration of nanoparticles dispersed in the glass particle, and is thus difficult to obtain strong luminescence and high fluorescence quantum yield.

In the third known production method, only one semiconductor nanoparticle can be contained in one glass particle. Therefore, the concentration of nanoparticles in the glass particle is extremely low, and it is difficult to obtain strong luminescence and high fluorescence quantum yield.

The present inventors carried out extensive research considering the above points. As a result, the inventors' reverse micelle methods have developed a novel production process that uses a reverse micelle process as in the above first known product method but comprises mixing semiconductor nanoparticles and a partially hydrolyzed alkoxide having an increased viscosity; incorporating the resulting product into reverse micelles produced using a nonionic surfactant; and further hydrolyzing the alkoxide to form a sol-gel glass.

This method allows for a shorter reaction time than known methods, thus producing glass particles in which nanoparticles are dispersed before deterioration of the nanoparticles. This method can also prevent semiconductor nanoparticles in reverse micelles from being removed from a silica network structure, thus preventing the semiconductor nanoparticles from being intensively present near the outer surface of small glass particles, and enabling the semiconductor nanoparticles to be dispersed and fixed inside of the small glass particles. As a result, this method can produce semiconductor-nanoparticle-dispersed small glass particles that emit bright fluorescent light with much higher fluorescence quantum yield (a maximum of 60% or more) than known particles.

More specifically, the present invention provides the following semiconductor-nanoparticle-dispersed small glass particles, and production processes thereof.

Item 1. Semiconductor-nanoparticle-dispersed small glass particles comprising small silica glass particles comprising a hydrolyzed alkoxide and having a mean particle size of not less than 10 nanometers and not more than 5 micrometers; and semiconductor nanoparticles dispersed in the small silica glass particles in a concentration of not less than $2 \times 10^{-5}$ mol/l and not more than $1 \times 10^{-2}$ mol/l, the semiconductor-nanoparticle-dispersed small glass particles emitting fluorescent light with a fluorescence quantum yield (quantum efficiency) of 25% or more, when dispersed in a solution.

Item 2. Semiconductor-nanoparticle-dispersed small glass particles according to Item 1, which contain more than one semiconductor nanoparticle per small silica glass particle on the average.

Item 3. Semiconductor-nanoparticle-dispersed small glass particles according to Item 1 or 2 which emit fluorescent light with a fluorescence quantum yield (quantum efficiency) of 60% or more, when dispersed in a solution.

Item 4. Semiconductor-nanoparticle-dispersed small glass particles according to any one of Items 1 to 3 wherein the semiconductor nanoparticle is at least one member selected from the group consisting of cadmium sulfide, zinc selenide, cadmium selenide, zinc telluride, cadmium telluride, zinc sulfide, and lead sulfide.

Item 5. Semiconductor-nanoparticle-dispersed small glass particles according to any one of Items 1 to 4 having at least one functional group selected from the group consisting of amino, thiol, and carboxyl groups on the surfaces of the small glass particles.

Item 6. A process for preparing semiconductor-nanoparticle-dispersed small glass particles comprising:
a first step of adding an alkoxide to a semiconductor-nanoparticle-dispersed aqueous solution to produce a sol-gel reaction solution containing a partially hydrolyzed alkoxide;
a second step of adding a surfactant to a hydrophobic organic solvent to produce a reverse micelle solution; and
a third step of mixing the solution obtained in the first step and the solution obtained in the second step to produce small glass particles containing semiconductor nanoparticles dispersed therein.

Item 7. A process according to Item 6 further comprising adding an aqueous alkaline solution to the semiconductor-nanoparticle-dispersed aqueous solution in the first step.

Item 8. A process according to Item 7 wherein the alkaline aqueous solution is aqueous ammonia or an aqueous sodium hydroxide solution.

Item 9. A process according to Item 7 or 8 wherein the alkaline aqueous solution contains a metal ion that is a component of the semiconductor nanoparticles.

Item 10. A process according to any one of Items 7 to 9 further comprising adding a surfactant for coating the semiconductor nanoparticles in the first step.

Item 11. A process according to Item 10 wherein the surfactant for semiconductor nanoparticle surfaces is thioglycolic acid.

Item 12. A process according to any one of Items 6 to 11 wherein the alkoxide is a compound represented by formula (I):

$$R^1{}_r\!\!-\!\!Si(OR^2)_{4-r} \tag{I}$$

wherein $R^1$ and $R^2$ represent lower alkyl groups that may be the same or different, and r represents 0, 1, 2, or 3.

Item 13. A process according to any one of Items 6 to 12 wherein the semiconductor-nanoparticle-dispersed aqueous solution is an aqueous solution in which at least one semiconductor nanoparticle selected from the group consisting of cadmium sulfide, zinc selenide, cadmium selenide, zinc telluride, cadmium telluride, zinc sulfide, and lead sulfide is dispersed.

Item 14. A process according to any one of Items 6 to 13 wherein the semiconductor nanoparticle is cadmium telluride.

Item 15. A process according to any one of Items 6 to 14 wherein the hydrophobic organic solvent is a hydrocarbon having 4 to 12 carbon atoms.

Item 16. A process according to any one of Items 6 to 14 wherein the hydrophobic organic solvent is cyclohexane.

Item 17. A process according to any one of Items 6 to 16 wherein the surfactant is a polyoxyethylene ether-based nonionic surfactant.

Item 18. A process according to any one of Items 6 to 17 wherein the alkoxide is tetraethoxysilane (TEOS).

Item 19. A process according to any one of Items 6 to 18, comprising, in addition to the first to third steps, a fourth step of adding alkoxide and an aqueous alkaline solution to a solution of the small glass particles obtained in the third step.

Item 20. A process according to any one of Items 6 to 18, comprising in addition to the first to third steps, a fourth step of adding alkoxide, a silane coupling agent, and an aqueous alkaline solution to a solution of the small glass particles obtained in the third step, and stirring.

Item 21. Semiconductor-nanoparticle-dispersed small glass particles produced by the process of any one of Items 6 to 20.

Item 22. A fluorescent material containing the semiconductor-nanoparticle-dispersed small glass particles of Item 1, 2, 3, 4, 5, or 21.

Item 23. A method for identifying small glass particles comprising placing on a stage a sample comprising a substrate and the semiconductor-nanoparticle-dispersed small glass particles of Item 1, 2, 3, 4, 5, or 21 dispersed and fixed on the substrate; and irradiating the sample with a laser beam and determining the spectrum of fluorescent light emitted from each semiconductor-nanoparticle-dispersed small glass particle on the substrate using a spectroscope, while moving the stage little by little to change the position irradiated with the laser beam.

The present invention is described in detail below.

The semiconductor-nanoparticle-dispersed small glass particles according to the invention comprise a spherical silica glass as a matrix, and semiconductor nanoparticles dispersed therein.

Semiconductor Nanoparticles

Examples of semiconductor nanoparticles include II-VI semiconductors that emit light in the visible to near-infrared regions, such as cadmium sulfide (CdS), zinc selenide (ZnSe), cadmium selenide (CdSe), zinc telluride (ZnTe), cadmium telluride (CdTe), zinc sulfide (ZnS), lead sulfide (PbS), and the like. Cadmium telluride and zinc selenide are particularly preferable.

The semiconductor nanoparticle may comprise an alloy of two or more types of semiconductors. Examples of alloys that can be preferably used include an alloy of zinc selenide and zinc telluride ($ZnSe_{1-x}Te_x$), an alloy of zinc selenide and cadmium selenide ($Zn_{1-y}Cd_ySe$), an alloy of zinc sulfide and cadmium sulfide ($Zn_{1-z}Cd_zS$), and the like. In the above formulas, $0<x<1$, $0<y<1$, and $0<z<1$. By appropriately selecting the ratio of two or more semiconductors contained in such an alloy, the band gap of semiconductor nanoparticles can be controlled and the fluorescence emission wavelength can be adjusted. Furthermore, semiconductor nanoparticles with a uniform particle size, shape, etc. can be obtained, which may result in a narrow emission spectrum to obtain highly monochromatic fluorescence.

The semiconductor nanoparticle may have a core-shell structure. The combination of metals for the core and the shell is not particularly limited. Materials of the core/shell may be, for example, any combination of one type of II-VI semiconductor/one type of II-VI semiconductor; one type of II-VI semiconductor/an alloy of two or more types of II-VI semiconductors; an alloy of two or more types of II-VI semiconductors/one type of II-VI semiconductor; and an alloy of two or more types of II-VI semiconductors/an alloy of two or more types of II-VI semiconductors.

In the present invention, semiconductor nanoparticles capable of being monodisperse in water and emitting light with a fluorescence quantum yield of 25% or more are preferably used. Monodisperse semiconductor nanoparticles are well mixed with and dispersed in water. Therefore, when a glass is produced by a sol-gel process, such semiconductor nanoparticles can be monodisperse in a silica glass under appropriate conditions, without aggregation. The maximum fluorescence quantum yield of the obtained small glass particles usually does not exceed the fluorescence quantum yield of the semiconductor nanoparticles contained therein. Therefore, when the fluorescence quantum yield of the semiconductor nanoparticles is low, i.e., less than 25%, it is necessary to increase the excitation light intensity to enable the glass particles to achieve a certain brightness, and it is thus not suitable for practical use.

In this specification, the term "fluorescence quantum yield" is defined as a ratio ($\Phi_{PL}/\Phi_A$) of the number of photons ($\Phi_{PL}$) emitted as fluorescent light (photoluminescence) to the number of photons ($\Phi_A$) absorbed. The fluorescence quantum yield is a value normally used in this technical field, and is synonymous with the term "internal quantum yield". The fluorescence quantum yield is determined by using a dye molecule whose fluorescence quantum yield is known, and comparing the absorbance and emission intensity of a solution of the dye molecule and those of a measurement target at an excitation light wavelength. In the measurement, comparison is usually made between a solution of the dye molecules and the measurement target with the same absorbance at the excitation wavelength (see, for example, known methods described in Dawson, et al., Journal of Physical Chemistry, vol. 72, p. 3251 (1968), Murase et al., Abstracts for the 2004 Annual Meeting of the Ceramic Society of Japan 2K35, and references therein).

Such semiconductor nanoparticles that are capable of being monodisperse in water and emitting bright fluorescent light with a fluorescence quantum yield of 25% or more can be produced, for example, by an aqueous solution method of Li, Murase, Chemistry Letters, vol. 34, page 92 (2005), improved from Rogach et al., Berichte der Bunsen-Gesellschaft fuer Physikalische Chemie, vol. 100, page 1772 (1996).

This method produces cadmium telluride nanoparticles by adding thioglycolic acid as a surfactant to an aqueous cadmium perchlorate solution adjusted to pH 11 to 12, particularly preferably pH 11.4 in such an amount to achieve a molar ratio of thioglycolic acid/cadmium of about 1.25, introducing hydrogen telluride or sodium hydrogen telluride under an inert atmosphere, followed by refluxing. Semiconductor nanoparticles other than cadmium telluride, such as zinc selenide, cadmium selenide, and zinc telluride; and alloys thereof (such as an alloy of zinc telluride and zinc selenide, an alloy of cadmium selenide and zinc selenide) can also be produced by a similar method, using the starting materials appropriate for the intended nanoparticle composition.

When such semiconductors of different chemical compositions are used, other surfactants can be used according to the chemical composition to enhance the fluorescence quantum yield. For example, when zinc selenide nanoparticles are produced, thioglycerol can be used in place of thioglycolic acid. If necessary, the nanoparticle surfaces are coated with another semiconductor to reduce the surface defects of the nanoparticles and enhance the fluorescence quantum yield.

The II-VI semiconductor nanoparticles capable of being monodisperse in water can also be produced according to the methods described in WO 00/17655, WO 00/17656, WO 2004/000971, etc. In such a method, nanoparticles are first produced by an organometallic process. More specifically, an organometallic compound (a compound in which an alkyl group is directly chemically bonded to a metal, such as dimethyl cadmium) is injected at a high temperature, i.e., about 300° C., into an organophosphorus compound (a compound in which an alkyl group is directly chemically bonded to phosphorus, such as trioctyl phosphine, or trioctyl phosphine oxide) to obtain semiconductor nanoparticles. If necessary, the surfaces of the nanoparticles are coated with another semiconductor. Subsequently, molecules containing both a hydrophobic group such as thiol and a hydrophilic group such as carboxyl are bonded to the nanoparticle surface to produce semiconductor nanoparticles that are capable of being monodisperse in water.

When semiconductor nanoparticles are produced by the above methods, the particle size determines the emission color. Particles with a smaller mean particle size emit light of a shorter wavelength. In general, the mean particle size of the semiconductor particles is preferably in the range of about 2 to about 8 nm (particularly preferably about 3 to about 7 nm). The particle size can be controlled by the reflux time. To obtain monochromatic light emission, the reflux time is controlled so that the standard deviation of the particle size distribution of the semiconductor nanoparticles is not more than 20% of the mean particle size. When the standard deviation of the particle size distribution is more than 20%, various light emissions are mixed, and it becomes difficult to obtain the color tone required of a display material. Therefore, a deviation of more than 20% is not preferable.

The process for preparing semiconductor-nanoparticle-dispersed fluorescent glass particles comprises: a first step of adding an alkoxide (and optionally an aqueous alkaline solution) to a semiconductor-nanoparticle-dispersed aqueous solution to produce a sol-gel reaction solution containing a partially hydrolyzed alkoxide; a second step of adding a surfactant to a hydrophobic organic solvent to produce a reverse micelle solution; and a third step of mixing the solution obtained in the first step and the solution obtained in the second step to produce small glass particles; and optionally further comprises a fourth step of adding an alkoxide, a silane coupling agent, and an aqueous alkaline solution to a solution of the small glass particles obtained in the third step, and stirring.

These four steps are described below.

First Step

In the first step, an alkoxide is added to a semiconductor-nanoparticle-dispersed aqueous solution to produce a sol-gel reaction solution containing a partially hydrolyzed alkoxide and semiconductor nanoparticles. If necessary, an aqueous alkaline solution may be added.

The semiconductor-nanoparticle-dispersed aqueous solution used in the first step refers to an aqueous solution containing fluorescent light (photoluminescence)-emitting semiconductor nanoparticles uniformly dispersed therein.

Examples of such semiconductor nanoparticles include the above-mentioned II-VI semiconductors that emit light in the visible to near-infrared regions. Specific examples thereof include cadmium sulfide, zinc selenide, cadmium selenide, zinc telluride, cadmium telluride, and alloys thereof. Cadmium telluride and zinc selenide are particularly preferable. Such nanoparticles may have a core-shell structure as described above.

The semiconductor-nanoparticle-dispersed aqueous solution used in the first step usually contains semiconductor nanoparticles in a concentration of about $5 \times 10^{-7}$ to $1 \times 10^{-3}$ mol/l, preferably about $5 \times 10^{-7}$ to $5 \times 10^{-4}$ mol/l, more preferably about $1 \times 10^{-6}$ to $5 \times 10^{-4}$ mol/l, most preferably about $1 \times 10^{-6}$ to $2 \times 10^{-4}$ mol/l.

The semiconductor nanoparticles are used in an amount to achieve a concentration of not less than $2 \times 10^{-5}$ mol/l and not more than $1 \times 10^{-2}$ mol/l, preferably not less than $2 \times 10^{-5}$ mol/l and not more than $4 \times 10^{-3}$ mol/l, and more preferably not less than $2 \times 10^{-4}$ mol/l and not more than $4 \times 10^{-3}$ mol/l, in the final product small silica glass particles.

In the first step, the semiconductor-nanoparticle-dispersed aqueous solution is mixed with an aqueous solution of an alkoxide. The alkoxide used herein is represented by formula (I):

$$R^1{}_r\!-\!Si(OR^2)_{4-r} \qquad (I)$$

wherein $R^1$ and $R^2$ represent lower alkyl groups that may be the same or different, and r represents 0, 1, 2, or 3.

Among the compounds represented by formula (I), compounds wherein r is 0, 1 or 2 are preferably used, and those wherein r is 0 or 1 are particularly preferable.

Examples of lower alkyl groups represented by $R^1$ and $R^2$ include linear and branched alkyl groups having 1 to 6 carbon atoms. Specific examples thereof include methyl, ethyl, n-propyl, isopropyl, and the like. Methyl and ethyl groups are particularly preferable.

Examples of preferable compounds represented by formula (I) include tetramethoxysilane, tetraethoxysilane (TEOS), tetraisopropoxysilane, methyltrimethoxysilane, ethyltrimethoxysilane, and the like. TEOS is particularly preferable.

Alkoxide is used in an amount such that the number of moles of alkoxide:the number of moles of semiconductor nanoparticles, calculated from the number of semiconductor nanoparticles, is about 1000:1 to about 1:1, and preferably about 100:1 to about 10:1. The number of moles of semiconductor nanoparticles, calculated from the number of semiconductor nanoparticles means that the value obtained by dividing the number of semiconductor nanoparticles by Avogadro's number is used as the number of moles of semiconductor nanoparticles.

In the aqueous alkoxide solution, the mixing ratio (molar ratio) of alkoxide to water is usually about 1:5 to about 1:500, preferably about 1:10 to about 1:300, and more preferably about 1:15 to about 1:200.

In the first step, alkoxide is partially hydrolyzed in an aqueous solution of semiconductor nanoparticles and alkoxide obtained by mixing as described above. Such partial hydrolysis of alkoxide is achieved by stirring the aqueous solution of semiconductor nanoparticles and alkoxide.

If necessary, an aqueous alkaline solution may be added. Any aqueous alkaline solution with pH 8 or more (preferably pH 9 to pH 12) can be used. Examples of aqueous alkaline solutions that can be preferably used include aqueous ammonia, and aqueous solutions of alkali metal hydroxides, such as sodium hydroxide and potassium hydroxide. The partial hydrolysis of alkoxide can be promoted by using such an aqueous solution. The use of aqueous ammonia or an aqueous solution of sodium hydroxide is particularly preferable.

The amount of aqueous alkaline solution is not particularly limited. For example, the aqueous alkaline solution may be added in an amount such that the resulting semiconductor-nanoparticle-dispersed aqueous solution has a pH of about 8 to about 11 (preferably a pH of about 8.5 to about 10).

In addition to such an aqueous alkaline solution, a metal ion that is a component of the semiconductor nanoparticles and/or a surfactant for coating the semiconductor nanoparticles may be added.

Examples of such metal ions include the above-mentioned metal ions of the semiconductor nanoparticles. Specific examples thereof include zinc ions and cadmium ions.

Any surfactant that is capable of coating the surfaces of semiconductor nanoparticles can be used as the surfactant for coating semiconductor nanoparticles, which may be added in the first step. More specifically, at least one member selected from thioglycolic acid, thioglycerol, 2-mercaptoethylamine, and glycine may be used as the surfactant. Among these, thioglycolic acid is preferable.

Addition of such metal ions and/or surfactant can prevent the release of the surfactant from the surfaces of semiconductor nanoparticles and the dissolution of semiconductor nanoparticles in an aqueous solution, thus inhibiting the deterioration of the nanoparticles.

In the first step, it is necessary to obtain a solution containing a partially hydrolyzed alkoxide, not a completely hydrolyzed alkoxide. This is because by using a partially hydrolyzed alkoxide having a higher viscosity than unreacted alkoxide, semiconductor nanoparticles can be incorporated into reverse micelles in the third step, and the alkoxide is then rapidly hydrolyzed to form a glass. If the alkoxide is hydrolyzed excessively in the first step, a glass is formed before the semiconductor nanoparticles are incorporated into reverse micelles, and it becomes impossible to control the size of the final product small glass particles by the reverse micelle size.

In the first step, the stirring temperature is not particularly limited. The stirring temperature is usually about room temperature, for example, about 5 to about 50° C., and preferably about 10 to about 40° C. The partial hydrolysis time (stirring time) of alkoxide in the first step is not particularly limited. The partial hydrolysis time is usually 1 to 6 hours, and preferably 2 to 4 hours. If the solution temperature at the time of stirring is too high, alkoxide is hydrolyzed so rapidly that it is difficult to obtain a solution of partially hydrolyzed alkoxide. If the solution temperature at the time of stirring is too low, alkoxide is hydrolyzed so slowly that it takes a long time to obtain a partially hydrolyzed alkoxide. As a result, the semiconductor nanoparticles gradually deteriorate during such long-term stirring, thus resulting in reduced fluorescence quantum yield.

The stirring of the solution in the first step is necessary to uniformly hydrolyze the alkoxide in the solution and uniformly mix the partially hydrolyzed alkoxide and semiconductor nanoparticles.

Second Step

In the second step, a surfactant is added to a hydrophobic organic solvent to form a reverse micelle solution.

Examples of hydrophobic organic solvents used in the second step include hydrocarbons having 4 to 12 carbon atoms. Specific examples thereof include linear, branched, or cyclic aliphatic hydrocarbons having 4 to 12 carbon atoms, and aromatic hydrocarbons having 6 to 12 carbon atoms. Such aliphatic hydrocarbons may be saturated or unsaturated as long as the aliphatic hydrocarbons have a melting point and a boiling point out of the range of 10 to 35° C. and are liquids at room temperature. Linear, branched, or cyclic saturated aliphatic hydrocarbons having 5 to 10 carbon atoms are preferable. Specific examples thereof include pentane, cyclopentane, hexane, cyclohexane, heptane, isoheptane, octane, isooctane, nonane, decane, and the like. Cyclohexane and isooctane are particularly preferable. The above aromatic hydrocarbons are monocyclic or bicyclic aromatic hydrocarbons, and may have an aliphatic hydrocarbon group on the aromatic ring. Specific examples thereof include benzene, toluene, and xylene, and the like.

Any surfactant that dissolves in a hydrophobic organic solvent and is capable of forming the so-called "reverse micelle" solution, in which the hydrophobic groups of the surfactant are directed outward and the hydrophilic groups of the surfactant are directed inward, can be used as the surfactant in the second step.

Examples of such surfactants include ionic (cationic, anionic or ampholytic (amphoteric)) surfactants whose hydrophilic groups and hydrophobic groups have an electric charge, and nonionic surfactants whose hydrophilic groups and hydrophobic groups have no electric charge.

Examples of ionic (anionic) surfactants include sodium bis(2-ethylhexyl)sulfosuccinate (trade name: "Aerosol OT", a product of Wako Pure Chemical Industries, Ltd.), and the like.

Examples of nonionic surfactants include polyoxyethylene ether-based nonionic surfactants. Specific examples thereof include polyoxyethylene alkyl phenyl ether-based nonionic surfactants. Among them, preferable are polyoxyethylene nonylphenyl ether-based nonionic surfactants, such as polyoxyethylene (5) nonylphenyl ether (tradename: "Igepal CO-520", a product of Aldrich), polyoxyethylene (2) nonylphenyl ether (tradename: "Igepal CO-210", a product of Aldrich), polyoxyethylene (9) nonylphenyl ether (tradename: "Igepal CO-630", a product of Aldrich), polyoxyethylene (12) nonylphenyl ether (tradename: "Igepal CO-720", a product of Aldrich), and the like; and polyoxyethylene isooctylphenyl-based ether nonionic surfactants, such as polyoxyethylene (2) isooctylphenyl ether (tradename: "Igepal CA-210", a product of Aldrich), polyoxyethylene (5) isooctylphenyl ether (tradename: "Igepal CA-520", a product of Aldrich), polyoxyethylene (12) isooctylphenyl ether (tradename: "Igepal CA-720", a product of Aldrich), and the like.

The number described after polyoxyethylene in the parentheses refers to the number of repetition of oxyethylene units.

Examples of preferable surfactants are nonionic surfactants, more preferably polyoxyethylene ether-based nonionic surfactants, even more preferably polyoxyethylene nonylphenyl ether-based nonionic surfactants, and particularly preferably polyoxyethylene (5) nonylphenyl ether. These are preferable because electrostatic repulsion does not occur between the reverse micelles and nanoparticles as described above, thus allowing the nanoparticles to be uniformly incorporated into the reverse micelles easily.

The reverse micelles are produced by adding a surfactant to a hydrophobic organic solvent and stirring. The amount of surfactant used is usually about 0.001 to about 0.1 moles, and preferably about 0.005 to about 0.02 moles, per mole of the hydrophobic organic solvent. The stirring temperature is not particularly limited but usually about 10 to 35° C. To form reverse micelles with a uniform size, it is necessary to vigorously stir the solution. Reverse micelles with a mean particle size (outer diameter) of about 10 nm to about 5 µm can be thereby formed. The mean particle size (outer diameter) of the reverse micelles can be changed by the proportions of surfactant, water, and hydrophobic organic solvent.

In the second step, the stirring temperature is not particularly limited. The stirring temperature is usually about room temperature, i.e., about 5 to about 50° C., and preferably about 10 to about 40° C.

Third Step

In the third step, the reverse micelle solution obtained in the second step, and the solution of partially hydrolyzed alkoxide and semiconductor nanoparticles obtained in the first step are mixed to incorporate partially hydrolyzed alkoxide and semiconductor nanoparticles into the reverse micelles, and then alkoxide is further hydrolyzed and the sol-gel reaction is allowed to proceed, thus providing small glass particles containing semiconductor nanoparticles dispersed therein.

To uniformly incorporate partially hydrolyzed alkoxide and semiconductor nanoparticles into reverse micelles, it is necessary to vigorously stir the solution. The mixture is thereby absorbed into the reverse micelle of a surfactant (for example, a polyoxyethylene ether-based nonionic surfactant, particularly "Igepal CO-520", or the like), and the sol-gel reaction is allowed to proceed in the reverse micelles.

In the first known production method mentioned above, after unhydrolyzed alkoxide and semiconductor nanoparticles are incorporated into reverse micelles, alkoxide is hydrolyzed and the sol-gel reaction is allowed to proceed, thus providing glass particles containing semiconductor nanoparticles dispersed therein. However, in this method, it is necessary to keep stirring the solution for 1 to 3 days to hydrolyze alkoxide to form a glass. In such long-term stirring, semiconductor nanoparticles deteriorate, resulting in reduced fluorescence quantum yield. As a result, only glass particles with unsatisfactory fluorescence quantum yield are obtained.

In contrast, in the present invention, after partially hydrolyzed alkoxide and semiconductor nanoparticles are incorporated into reverse micelles, alkoxide is hydrolyzed and the sol-gel reaction is allowed to proceed, thus providing small glass particles containing semiconductor nanoparticles dispersed therein, which shortens the reaction time. As a result, deterioration of the semiconductor nanoparticles is suppressed, and small glass particles with extremely high fluorescence quantum yield can be obtained.

In the preparation process of the invention, the glass formation in reverse micelles initiates in the state in which alkoxide is already partially hydrolyzed, i.e., a silica network structure is partially formed to have a comparatively high viscosity and low fluidity. Therefore, undesirable states are unlikely to occur in the glass formation process. Such undesirable states are, for example, reduced concentration of semiconductor nanoparticles dispersed in the small glass particles, which is due to the semiconductor nanoparticles being expelled from the silica gel network structure and moved and fixed near the outer surface of the small glass particles; reduced fluorescence quantum yield due to the aggregation of the nanoparticles; and reduced long-term stability due to insufficient shielding of the nanoparticles from the external atmosphere.

Thus, the preparation process of the invention can advantageously produce small glass particles containing plural nanoparticles well dispersed therein, while preventing the nanoparticles from being intensively present near the outer surface of the glass particles.

The mixing ratio (molar ratio) of alkoxide and water is usually about 1:5 to about 1:500, preferably about 1:10 to about 1:300, and more preferably about 1:15 to about 1:200. Such a mixing ratio is preferable because when such a mixing ratio is used, a sufficient amount of water for hydrolysis is present, so that the total amount of alkoxide can be converted into a glass by a sol-gel reaction, and the rate of glass formation by the sol-gel reaction can also be appropriate.

In the third step, the stirring temperature is not particularly limited. The stirring temperature is usually about room temperature, i.e., 5 to 50° C., and preferably 10 to 40° C. The alkoxide hydrolysis time (stirring time) in the third step is not particularly limited. The alkoxide hydrolysis time is usually 1 to 6 hours, and preferably 2 to 4 hours.

Upon completion of the reaction, fluorescent glass particles incorporating semiconductor nanoparticles therein have been dispersed in a hydrophobic organic solvent. The solvent is then removed therefrom and, if necessary, an excess of surfactant adhering to the surfaces of the obtained glass particles is removed by washing with an appropriate solvent. For example, when the surfactant is a polyoxyethylene ether-based nonionic surfactant, solvents such as acetonitrile, toluene, and the like can be used. The resulting mixture is then dried to produce powder of substantially spherical fluorescent small glass particles ("spherical" includes, for example, a completely round ball, an oval ball, and like shapes; the same applied hereinafter) in which most of the semiconductor nanoparticles are present inside, and only some of the nanoparticles are fixed near the surfaces thereof. The obtained fluorescent glass particles have a mean particle size of about 10 nm to about 5 µm.

Fourth Step

A post-processing (fourth step) as described below may be optionally performed after the third step. The post-processing comprises adding an alkoxide such as TEOS to the reaction solution obtained in the third step, optionally adding an aqueous alkaline solution for hydrolyzing the added alkoxide, and stirring for 1 to 6 hours, and more preferably 3 to 5 hours.

The stirring temperature is not particularly limited. The stirring temperature is usually 5 to 70° C., and preferably 10 to 60° C. In the post-processing, ultrasonic vibration may be applied to the solution, and the solution may be warmed to about 35 to 70° C.

Such a post-processing is additionally performed for the following reason. If the semiconductor-nanoparticle-dispersed small glass particles in the solution immediately after the third step have some semiconductor nanoparticles fixed near the outer surfaces, reduction of fluorescent intensity with time may occur due to the ease of contact of such semiconductor nanoparticles with the external atmosphere, because the nanoparticles are coated only with a thin glass layer. Furthermore, immediately after the completion of the third step, sufficiently hard glass particles may not have been formed.

By adding alkoxide, represented by formula (I), to the solution of such semiconductor nanoparticle-dispersed small glass particles to hydrolyze alkoxide, a harder glass coating layer can be formed on the surfaces of the dispersed semiconductor nanoparticle-containing small glass particles immediately after the completion of the third step. In this step, adding an aqueous alkaline solution is preferable to promote the hydrolysis of alkoxide.

Examples of aqueous alkaline solutions are those described in the first step.

The amount of aqueous alkaline solution used is not particularly limited and can be appropriately selected according to the pH, etc. of the aqueous alkaline solution.

In addition to such an aqueous alkaline solution, a metal ion that is a component of the semiconductor nanoparticles and/or a surfactant for coating the semiconductor nanoparticles may be added.

Examples of such metal ions and surfactants are the same as those described in the first step. Aqueous ammonia or an aqueous sodium hydroxide solution is particularly preferable as the aqueous alkaline solution. Thioglycolic acid is preferable as the surfactant for coating the semiconductor nanoparticles. Substantially all the semiconductor nanoparticles are thereby dispersed and fixed in the small glass particles, thus providing small grass particles with only a small reduction in fluorescence intensity over time.

A glass layer can also be formed by adding to the alkoxide of formula (I) a compound represented of formula (II)

$$R^3{}_p\text{—Si}(OR^4)_{4-p} \qquad (II)$$

wherein $R^3$ represents a lower alkyl group having an amino group, a thiol group, or a carboxyl group, $R^4$ represents a lower alkyl group, and p represents 1, 2, or 3. The compounds represented by formula (II) are those in which an organic functional group represented by $R^3$, and an alkoxy group represented by $OR^4$ are both bonded to one silicon atom. Such specific alkoxides are collectively referred to as "silane coupling agents". Alternatively, after a grass layer is formed by treatment with an alkoxide represented by formula (I), a treatment with a silane coupling agent represented by formula (II) may be performed to form a second glass layer. Small glass particles that have a functional group other than OH groups on the surfaces can thereby be produced.

Among the silane coupling agents represented by formula (I), those wherein p=1 are preferably used.

Examples of lower alkyl groups represented by $R^3$ include linear or branched alkyl groups having 1 to 6 carbon atoms (particularly 3 carbon atoms). Specific examples thereof include methyl, ethyl, n-propyl, isopropyl, and the like, and n-propyl is particularly preferable. The lower alkyl groups represented by $R^3$ have at least one member selected from the group consisting of amino, thiol and carboxyl groups.

Examples of lower alkyl groups represented by $R^4$ include linear or branched alkyl groups having 1 to 6 carbon atoms. Specific examples thereof include methyl, ethyl, n-propyl, isopropyl, and the like. Methyl and ethyl are particularly preferable.

Among the silane coupling agents represented by formula (II), specific examples thereof include 3-aminopropyltrimethoxysilane and 3-mercaptopropyltrimethoxysilane, wherein p is 1.

The glass particles thus produced by using a silane coupling agent represented by formula (II) have a functional group such as —OH, —NH$_2$, —SH, and —COOH, and the like on the surfaces thereof. Therefore, the glass particles can be bonded to biomolecules via the functional group, and can be used as a fluorescent label.

In the post-processing, if alkoxide is added to the solution more slowly, semiconductor-nanoparticle-dispersed small glass particles with a comparatively small particle size are obtained; and if alkoxide is added to the solution more rapidly, semiconductor nanoparticle-dispersed small glass particles with a comparatively large particle size are obtained. This is considered to be for the following reason. When alkoxide is slowly added to the solution, each of the core semiconductor-nanoparticle-dispersed small glass particles are independently coated with a glass layer. In contrast, when alkoxide is rapidly added to the solution, a group of some of the core semiconductor-nanoparticle-dispersed small glass particles are coated together with a glass layer, thus providing final glass particles with an increased particle size.

In the post-processing, ultrasonic vibration may be applied to the solution and/or the solution may be warmed to increase the rate of glass formation by hydrolysis of the alkoxide in the post-processing and shorten the post-processing time, thereby preventing the semiconductor nanoparticles from deterioration during post-processing. However, if the solution is excessively heated in the post-processing, the nanoparticles incorporated in glass particles with an insufficient hardness obtained by the third step may thermally decompose or aggregate, and the nanoparticles may also thermally aggregate and deteriorate. Therefore, the temperature at which the solution is warmed is 35 to 70° C., and preferably 40 to 60° C.

Upon completion of the reaction after the post-processing, fluorescent glass particles incorporating semiconductor nanoparticles therein are dispersed in a hydrophobic organic solvent. The solvent is then removed therefrom and, if necessary, an excess of surfactant adhering to the surfaces of the obtained glass particles is removed by washing with an appropriate solvent. For example, when the surfactant is a polyoxyethylene ether-based nonionic surfactant, acetonitrile, toluene, or the like may be used as the solvent. The resulting particles are then dried to thereby produce powder of substantially spherical fluorescent small glass particles incorporating the semiconductor nanoparticles therein.

According to the semiconductor-nanoparticle-dispersed small glass particles of the invention, when the concentration of semiconductor nanoparticles in small silica glass particles is not less than $2\times10^{-5}$ mol/l and not more than $1\times10^{-2}$ mol/l (particularly not less than $2\times10^{-5}$ mol/l and not more than $4\times10^{-3}$ mol/l), the semiconductor-nanoparticle-dispersed small glass particles contain more than one semiconductor nanoparticle (preferably 1.5 or more, particularly 2 or more semiconductor nanoparticles) per small silica glass particle on the average.

For example, when the concentration of semiconductor nanoparticles in small silica glass particles with a diameter of 10 nm is $4\times10^{-3}$ mol/l, the semiconductor-nanoparticle-dispersed small glass particles contain about 1.5 semiconductor nanoparticles per small glass particle on the average.

When the concentration of semiconductor nanoparticles in small silica glass particles with a diameter of 30 nm is $2\times10^{-4}$ mol/l to $4\times10^{-3}$ mol/l, the semiconductor-nanoparticle-dispersed small glass particles contain about 2 to about 40 semiconductor nanoparticles per small glass particle on the average.

When the concentration of semiconductor nanoparticles in small silica glass particles with a diameter of 60 nm is $2\times10^{-5}$ mol/l to $4\times10^{-3}$ mol/l, the semiconductor-nanoparticle-dispersed small glass particles contain about 1.6 to about 320 semiconductor nanoparticles per small glass particle on the average.

When the concentration of semiconductor nanoparticles in small silica glass particles with a diameter of more than 90 nm is the lower limit of the above range (i.e., $2\times10^{-5}$ mol/l) or more, the semiconductor nanoparticle-dispersed small glass particles contain about 5 or more semiconductor nanoparticles per small glass particle on the average.

When the concentration of semiconductor nanoparticles in the small glass particles is lower than the above-mentioned range, sufficiently bright luminescence cannot be obtained. Therefore, it is not suitable for practical use.

The mean particle size of the obtained fluorescent small glass particles is about 10 nm to about 5 μm, particularly 20 nm to 1 μm. The particle size distribution of the fluorescent small glass particles can be regulated by centrifugation, filtration, etc.

When the thus-obtained semiconductor nanoparticle-dispersed small glass particles are dispersed in a solution, the particles emit fluorescence with a fluorescence quantum yield (quantum efficiency) of 25% or more in the visible to near-infrared regions, particularly the visible wavelength region (usually a wavelength region of 360 to 830 nm, and particularly 400 nm to 760 nm), preferably 35% or more, and more preferably 60% or more. The glass-particle-dispersed solution used to determine the fluorescence quantum yield is usually a solution obtained after the third step or fourth step. Thus, a hydrophobic organic solvent (such as cyclohexane or like hydrocarbon solvents) is usually used as the solvent. Alternatively, water may be used as the solvent to determine the fluorescence quantum yield. The fluorescence quantum yield is usually constant, irrespective of the concentration of the glass particles in the solution.

The fluorescence quantum yield is determined by placing the glass-particle-dispersed solution into a quartz cell and calculating the fluorescence quantum yield from the fluorescence spectrum and absorption spectrum obtained using a usual spectrofluorimeter and absorption spectrophotometer.

Thus, the preparation process of the invention forms a glass by incorporating a mixture of partially hydrolyzed alkoxide and semiconductor nanoparticles using a combination of a reverse micelle process and a sol-gel process, and is a highly effective method for obtaining a fluorescent glass particles with high fluorescence quantum yield. In particular, the preparation process of the invention has advantages in that the production steps are simple, and semiconductor nanoparticles can be contained in small glass particles without substantially reducing the fluorescence quantum yield (quantum efficiency) of the semiconductor nanoparticles of the semiconductor-nanoparticle-dispersed aqueous solution used in the first step.

Moreover, according to the present invention, the semiconductor nanoparticles can be fixed inside the glass particles as well as on the surfaces thereof. Therefore, the fluorescence quantum yield of the semiconductor nanoparticles can be maintained for a long period of time, irrespective of the external environment.

Furthermore, when a powder of the fluorescent small glass particles containing the semiconductor nanoparticles dispersed and fixed therein is formed into a predetermined shape and optionally heated (calcined), a fluorescent material (fluorescent glass material) containing the semiconductor nanoparticles dispersed and fixed therein can be obtained.

Because the glass particles emit such strong light, light can be extracted from each glass particle to determine the spectrum thereof. Based on the spectroscopy results, small particles mainly incorporating red-emitting semiconductor nanoparticles, those mainly incorporating green-emitting semiconductor nanoparticles, and those incorporating red-emitting semiconductor nanoparticles and green-emitting semiconductor nanoparticles can be identified. Examples of such identification methods include the single-particle spectrometer and method described in Murase, Chemical Physics Letters, vol. 368, page 76, 2003.

For example, semiconductor-nanoparticle-dispersed small glass particles can be identified by placing on a stage a sample comprising a substrate and the semiconductor-nanoparticle-dispersed small glass particles dispersed and fixed on the substrate, then irradiating the sample with a laser beam emitted from a light source or a laser beam emitted from a light source and condensed by a lens and determining the spectrum of fluorescent light emitted from each semiconductor-nanoparticle-dispersed small glass particle on the substrate using a spectroscope, while moving the stage little by little to change the position irradiated with the laser beam.

More specifically, a sample is prepared by dispersing small glass particles incorporating nanoparticles having different fluorescence spectra on a non-fluorescent quartz glass plate in such a concentration that about 10 nanoparticles are present per 10 μm×10 μm of the plate. This sample is irradiated with an argon laser beam of a short wavelength (488 nm) condensed by a ×40 objective lens, and a spectrum of fluorescent light emitted therefrom is obtained using a CCD spectrometer system. In the observation, such glass particles can be found by detecting fluorescence while scanning the glass plate at the position irradiated with an argon laser using an X-, Y-micrometer. Small glass particles incorporating semiconductor nanoparticles having different fluorescence emission spectra can be thereby identified according to the color of the emitted fluorescence.

When a silane coupling agent represented by formula (II) is added in the fourth step of the small glass particle production process, a functional group, such as an amino, thiol, or carboxyl group, is bonded to the surfaces of the small glass particles. The glass particles can be bonded to biomolecules via such a functional group and used as a fluorescent label. Specific cells that contain such biomolecule-bonded glass particles can be selectively isolated using flow cytometry.

Effect of the Invention

The semiconductor nanoparticle-dispersed small glass particles of the invention can emit various colors in the visible to near-infrared regions, particularly in the visible region, under UV radiation of the same wavelength according to the composition and particle size of the dispersed nanoparticles, when the particles are dispersed in a solution or formed into a powder by distilling off the solvent. The semiconductor-nanoparticle-dispersed small glass particles emit light with a fluorescence quantum yield of at least 25%, more preferably 60% or more, which is remarkably high, compared to known particles, and contain plural nanoparticles per glass particle, i.e., contains nanoparticles in a high concentration, thus providing increased fluorescence intensity. Furthermore, the semiconductor-nanoparticle-dispersed small glass particles as a whole basically have glass characteristics, and thus have excellent chemical stability against the external atmosphere, excellent mechanical strength, excellent heat resistance, etc., thus having excellent long-term stability of fluorescence characteristics.

The present invention further provides a process for producing fluorescent small glass particles that emit fluorescent light with high fluorescence quantum yield and has excellent long-term stability of fluorescence characteristics, which are due to the presence of plural semiconductor nanoparticles dispersed and fixed inside a small glass particle, as described above.

BEST MODE FOR CARRYING OUT THE INVENTION

The following examples serve to illustrate the present invention, without, however, limiting the invention thereto.

Example 1

II-VI semiconductor cadmium telluride nanoparticles were prepared according to the method described in Li, Murase, Chemistry Letters, vol. 34, page 92 (2005). More specifically, while vigorously stirring an aqueous solution of cadmium perchlorate adjusted to pH 11.4, hydrogen telluride gas was allowed to react in the presence of thioglycolic acid ($HOOCCH_2SH$) as a surfactant under an argon gas atmosphere. Clusters of cadmium telluride were thereby produced in the aqueous solution, and this aqueous solution was refluxed under atmospheric pressure for 6 days, thus providing cadmium telluride nanoparticles having a mean particle size of 4 nm and emitting red light with an emission peak wavelength of 646 nm under UV excitation and with a fluorescence quantum yield of 81%.

The semiconductor nanoparticles thus obtained were dispersed and fixed in small glass particles by the combination of a reverse micelle process and a sol-gel process as described below.

First Step

While stirring about 2 ml of a solution produced by adding aqueous ammonia as an aqueous alkaline solution to the aqueous solution containing the cadmium telluride nanoparticles dispersed therein, $6.7 \times 10^{-4}$ mol of TEOS was added. The resulting solution was vigorously stirred at room temperature for 2 to 3 hours to partially hydrolyze the TEOS. Subsequently, this solution was centrifuged at 4000 rpm to isolate a transparent supernatant by removing a trace amount of precipitate. The supernatant emitted strong red fluorescent light under UV irradiation.

Second Step

Cyclohexane and polyoxyethylene (5) nonylphenyl ether (tradename: "Igepal CO-520", a product of Aldrich) were mixed in a molar ratio of 29:1, and stirred to form a solution.

Third Step

While stirring the cyclohexane solution of polyoxyethylene (5) nonylphenyl ether obtained in the second step at room temperature, the supernatant containing partially hydrolyzed TEOS and nanoparticles, obtained in the first step, was added dropwise and mixed. The obtained solution emitted strongish red fluorescent light under UV irradiation.

Fourth Step (Post-Processing Step)

Further, $1.3 \times 10^{-3}$ mol of TEOS was added to the solution. Subsequently, 100 µl of 6.25% aqueous ammonia as an aqueous alkaline solution was added dropwise and mixed. The resulting solution was stirred for another 4 hours. Further, ultrasonic vibration was applied to the obtained solution of cadmium telluride nanoparticle-dispersed small glass particles at room temperature for 30 minutes.

A solution of cadmium telluride nanoparticle-dispersed small glass particles was prepared in the above first to third steps and fourth step (post-processing step). This solution was centrifuged at 4000 rpm to separate a brown precipitate and a transparent supernatant. Both the precipitate and transparent supernatant emitted strong red fluorescent light under UV excitation.

TEM observation confirmed that the cadmium telluride nanoparticle-dispersed small glass particles were substantially spherical. The particle size (diameter) distribution of the cadmium telluride nanoparticle-dispersed small glass particles in the transparent supernatant was about 10 nm to about 300 nm. The mean particle size thereof was estimated to be about 20 to about 30 nm. The particle size (diameter) distribution of the cadmium telluride nanoparticle-dispersed small glass particles in the brown precipitate was about 50 nm to about 5 µm. Thus, the results show that the brown precipitate contained small glass particles having a particle size larger than those in the supernatant.

FIG. 1 shows a TEM photograph of cadmium telluride nanoparticle-dispersed glass particles contained in the supernatant. The photograph shows that many cadmium telluride nanoparticles (small black spots) are present inside the glass particles (dark gray circles) having a particle size of about 70 to about 100 nm. The photograph further shows that cadmium telluride nanoparticles are also present inside the glass particles having a particle size out of this range, for example, a particle size of about 20 to about 30 nm.

FIG. 2 shows a TEM photograph of cadmium telluride nanoparticle-dispersed glass particles contained in the brown precipitate.

The particle size of the cadmium telluride nanoparticle-dispersed glass particles in the transparent supernatant was also measured using a light scattering particle size analyzer ("Nanotrac 150", a product of Microtrac, Inc.). The results were almost the same as those obtained by the TEM observation.

The fluorescence spectrum of the red-fluorescent light-emitting transparent supernatant was almost the same as that of the semiconductor-nanoparticle-dispersed aqueous solution used as the starting material, and the emission peak wavelength was 642 nm. The fluorescence quantum yield was estimated to be 75%.

When TEOS was added more rapidly in the fourth step (post-processing step), the mean particle size of the small glass particles in the supernatant obtained by centrifugation increased to about 100 nm. Even in that case, the fluorescence quantum yield was 75%. The precipitates thus obtained by centrifugation were separated into small glass particles having a large particle size and those having a small particle size, using a filter having a pore size of 450 nm ("Milex", a product of Millipore).

In the fourth step (post-processing step), when ultrasonic vibration was applied for 30 minutes as described above and the solution was then warmed to 40° C. for 30 minutes, the red fluorescence quantum yield of the supernatant obtained by performing centrifugation in the same manner as above was 81%, i.e., the same value as the fluorescence quantum yield of the semiconductor-nanoparticle-dispersed aqueous solution used as the starting material.

FIG. 3 shows a red fluorescence spectrum (a) of the cadmium telluride nanoparticle-dispersed aqueous solution used as the starting material, and a red fluorescence spectrum (b) of the solution of the cadmium telluride nanoparticle-dispersed small glass particles obtained as a supernatant by performing centrifugation after the fourth step (post-processing step) comprising 30 minutes of ultrasonic vibration application and 30 minutes of treatment at 40° C.

Even when the fourth step (post-processing step) was not performed, a red-emitting precipitate and supernatant of cadmium telluride nanoparticle-incorporating small glass particles were obtained after centrifugation. The outlines of the glass particles were not so clear, and the fluorescence quantum yield was about 60 to about 70%, which is low, compared to the case in which the post-processing step was performed.

The fluorescence quantum yield was determined by placing the small glass particle-dispersed solution into a quartz cell and calculating the fluorescence quantum yield from the fluorescence spectrum and absorption spectrum obtained using a usual spectrofluorometer and absorption spectrophotometer. More specifically, the fluorescence quantum yield of the ultrafine particles was calculated in comparison with an aqueous sulfuric acid solution (sulfuric acid concentration: 0.5 mol/l) of a quinine molecule, whose absorbance (absorption coefficient×concentration×optical path length) and fluorescence quantum yield were known, according to a known process (Dawson, et al., Journal of Physical Chemistry, vol. 72, page 3251 (1968)). The same determination method is used hereinafter.

Further, the precipitate and the supernatant of the cadmium telluride nanoparticle-incorporating glass particles were washed with acetonitrile, and an excess of polyoxyethylene (5) nonylphenyl ether was removed. The solvent was then evaporated to dryness to provide a strong red fluorescence-emitting powder.

The cadmium telluride nanoparticle-dispersed small glass particles exhibited stability higher than cadmium telluride nanoparticles not dispersed in small glass particles. When the red fluorescence-emitting cadmium telluride nanoparticles were dispersed in an aqueous solution and allowed to stand in the air at room temperature for 2 months, the nanoparticles aggregated and precipitated in the aqueous solution, and stopped emitting fluorescence.

In contrast, when the red light-emitting cadmium telluride nanoparticle-dispersed small glass particles were dispersed in cyclohexane and allowed to stand in the air at room temperature for 2 months, the nanoparticles did not aggregate or precipitate in a solution thereof, and emitted strong red light. When the small glass particles were formed into a solid powder and allowed to stand in the same conditions as above, the powder emitted strong red light, and did not aggregate or precipitate in a solution thereof.

Example 2

II-VI semiconductor cadmium telluride nanoparticles were produced according to the method described in Li, Murase, Chemistry Letters, vol. 34, page 92 (2005). More specifically, while vigorously stirring an aqueous solution of cadmium perchlorate adjusted to pH 11.4, hydrogen telluride gas was allowed to react in the presence of thioglycolic acid ($HOOCCH_2SH$) as a surfactant under an argon gas atmosphere. Clusters of cadmium telluride were thereby formed in the aqueous solution, and the aqueous solution was refluxed under atmospheric pressure for 2 hours, thus providing cadmium telluride nanoparticles having a mean particle size of 3 nm and emitting green light with an emission peak wavelength of 548 nm under UV excitation and with a fluorescence quantum yield of 35%.

By performing the first to third steps and fourth step (post-processing step) in the same manner as in Example 1 using the semiconductor nanoparticles thus obtained, a solution of cadmium telluride nanoparticle-dispersed small glass particles was obtained. Ultrasonic vibration was applied to the obtained solution of the cadmium telluride nanoparticle-dispersed small glass particles at room temperature for 30 minutes. This solution was centrifuged at 4000 rpm to separate a brown precipitate and a transparent supernatant. Both the precipitate and supernatant emitted strong green fluorescent light under UV excitation.

TEM observation confirmed that the cadmium telluride nanoparticle-dispersed small glass particles were spherical. The particle size (diameter) distribution of cadmium telluride-nanoparticle-dispersed small glass particles in the transparent supernatant was about 10 nm to about 300 nm. The mean diameter thereof was estimated to be about 20 to about 30 nm. The particle size (diameter) distribution of the cadmium telluride nanoparticle-dispersed small glass particles in the brown precipitate was about 50 nm to about 5 µm. Thus, the results show that the brown precipitate contained glass fine particles having a particle size larger than those in the supernatant.

The particle size of the cadmium telluride nanoparticle-dispersed glass particles in the transparent supernatant was also measured using the above-mentioned light scattering particle size analyzer. The results were almost the same as those obtained by the TEM observation.

The fluorescence spectrum of the green fluorescence-emitting transparent supernatant was almost the same as that of the semiconductor nanoparticle-dispersed aqueous solution used as the starting material. The emission peak wavelength was 539 nm, and the fluorescence quantum yield was estimated to be 28%.

When TEOS was added more rapidly in the fourth step (post-processing step), the mean particle size of the small glass particles contained in the supernatant obtained by centrifugation was increased to about 100 nm. Even in that case, the fluorescence quantum yield was 28%. The precipitates thus obtained by centrifugation were separated into small glass particles having a large particle size and those having a small particle size, using a filter having a pore size of 450 nm ("Milex", a product of Millipore).

In the fourth step (post-processing step), when the solution was warmed at 40° C. for 30 minutes after the 30-minute ultrasonic vibration application, the green fluorescence quantum yield of the supernatant obtained by performing centrifugation in the same manner as above was 35%, i.e., the same value as the fluorescence quantum yield of the semiconductor nanoparticle-dispersed aqueous solution used as the starting material.

FIG. 4 shows a green fluorescence spectrum (a) of the cadmium telluride nanoparticle-dispersed aqueous solution used as the starting material, and a green fluorescence spectrum (b) of the solution of the cadmium telluride nanoparticle-dispersed small glass particles obtained as a supernatant by performing centrifugation after the fourth step (post-processing step) comprising 30 minutes of ultrasonic vibration application and 30 minutes of treatment at 40° C.

Even when the fourth step (post-processing step) was not performed, a green light-emitting precipitate and supernatant of cadmium telluride nanoparticle-dispersed small glass particles were obtained after centrifugation. The outlines of the glass particles were not so clear in the TEM photograph, and the fluorescence quantum yield was about 25 to about 30%, which is a low value, compared to the case in which the post-processing step was performed.

By further performing the procedures in the same manner as in Example 1, a strong green fluorescence-emitting powder was obtained.

The green light-emitting cadmium telluride nanoparticle-dispersed small glass particles exhibited stability higher than nanoparticles not dispersed in small glass particles, like the case of the red light-emitting dispersed cadmium telluride nanoparticle-incorporating small glass particles described in Example 1. When the green light-emitting cadmium telluride nanoparticles were dispersed in an aqueous solution and allowed to stand in the air at room temperature for 2 months, the nanoparticles aggregated and precipitated in the aqueous solution, and hardly emitted fluorescent light. In contrast, when the nanoparticle-dispersed small glass particles were dispersed in cyclohexane and allowed to stand under the same conditions as above, the nanoparticles did not aggregate or precipitate and maintained emission intensity. Even when the dispersed nanoparticle-dispersed small glass particles were formed into a solid powder, the emission intensity was maintained.

Example 3

II-VI semiconductor zinc selenide nanoparticles were produced according to the method described in Murase, Gao, Gaponik, Yazawa, Feldmann, International Journal of Modern Physics B, vol. 15, page 3881, (2001). More specifically, while vigorously stirring an aqueous solution of zinc perchlorate adjusted to pH 6.5, hydrogen selenide gas was allowed to react in the presence of thioglycolic acid ($HOOCCH_2SH$) as a surfactant under an argon gas atmosphere. Clusters of zinc selenide were thereby produced, and this aqueous solution was refluxed under atmospheric pressure for several tens of hours to produce zinc selenide nanoparticles having a mean particle size of 3 nm and emitting bluish violet fluorescent light under UV excitation.

To reduce the surface defects of the nanoparticles and enhance the fluorescence quantum yield, the zinc selenide nanoparticles were dispersed in an aqueous solution containing zinc ions and thioglycolic acid, then adjusted to pH 10 to 11 and subjected to UV irradiation to conduct post-processing. A core-shell nanoparticle comprising a zinc selenide nanoparticle as the core whose surface was coated with a zinc sulfide shell layer was thereby prepared. This core-shell nanoparticle emitted bluish violet light with an emission peak wavelength of 438 nm under UV excitation, and with a fluorescence quantum yield of 40%.

Using the thus obtained semiconductor nanoparticles, the first to third steps and fourth step (post-processing step) were performed in the same manner as in Example 1, except that in the first step and fourth step, an aqueous sodium hydroxide solution containing zinc ions and thioglycolic acid was used as the aqueous alkaline solution in place of aqueous ammonia. The aqueous sodium hydroxide solution was prepared by adding zinc perchlorate and thioglycolic acid to distilled water, and then gradually adding 1 mol/l of an aqueous sodium hydroxide solution to the distilled water to achieve a pH of about 10 to about 11.

As a result, a solution of zinc selenide-zinc sulfide core-shell nanoparticle-dispersed small glass particles was obtained. Both the precipitate and supernatant obtained by centrifugation at 4000 rpm emitted strong bluish violet fluorescent light.

FIG. 5 shows a TEM photograph of zinc selenide-zinc sulfide core-shell nanoparticle-dispersed small glass particles contained in the supernatant. The photograph shows that many zinc selenide-zinc sulfide core-shell nanoparticles (small black spots) are present inside the glass particles (dark gray circles) having a particle size of about 20 to about 50 nm.

The fluorescence spectrum of the bluish violet fluorescence-emitting transparent supernatant was not so different from that of the semiconductor-nanoparticle-dispersed aqueous solution used as the starting material. The emission peak wavelength was 432 nm, and the fluorescence quantum yield was estimated to be 27%.

FIG. 6 shows a bluish violet fluorescence spectrum (a) of the zinc selenide-zinc sulfide core-shell nanoparticle-dispersed aqueous solution used as the starting material, and a bluish violet fluorescence spectrum (b) of the solution of the zinc selenide-zinc sulfide core-shell nanoparticle-dispersed glass particle obtained as a supernatant by centrifugation.

The precipitate and the supernatant of the zinc selenide-zinc sulfide core-shell nanoparticle-incorporating glass particles were washed with acetonitrile, and an excess of polyoxyethylene (5) nonylphenyl ether was removed, and then the solvent was evaporated to dryness, thus providing a strong bluish violet fluorescence-emitting powder.

Example 4

II-VI semiconductor zinc selenide-cadmium selenide alloy nanoparticles were produced according to the method described in Li, Murase, Chemistry Letters, vol. 34, page 92 (2005). More specifically, while vigorously stirring an aqueous solution of a mixture of zinc perchlorate and cadmium perchlorate adjusted to pH 6.5, hydrogen selenide gas was allowed to react in the presence of thioglycolic acid (HOOCCH$_2$SH) as a surfactant under an argon gas atmosphere. Clusters containing zinc selenide and cadmium selenide were thereby produced in the aqueous solution, and this aqueous solution was refluxed under atmospheric pressure for several tens of hours to produce zinc selenide-cadmium selenide alloy nanoparticles having a mean particle size of 3 nm, and emitting blue light under UV excitation.

To reduce the surface defects of the zinc selenide-cadmium selenide alloy nanoparticles and enhance the fluorescence quantum yield, the zinc selenide-cadmium selenide alloy nanoparticles were dispersed in an aqueous solution containing zinc ions, cadmium ions, and thioglycolic acid, then adjusted to pH 10 to 11, and subjected to UV irradiation to perform post-processing. A core-shell nanoparticle comprising a zinc selenide-cadmium selenide alloy particle as the core whose surface was coated with a thin zinc sulfide/cadmium sulfide alloy shell layer was thereby prepared. This core-shell nanoparticle emitted blue light with an emission peak wavelength of 450 nm under UV excitation, and with a fluorescence quantum yield of 50%.

Using the thus obtained semiconductor nanoparticles, the first to third steps and the fourth step (post-processing step) were performed in the same manner as in Example 1 to produce a solution in which small glass particles incorporating core-shell nanoparticles comprising a zinc selenide-cadmium selenide alloy as the core and a zinc sulfide-cadmium sulfide alloy as the shell were dispersed. Both the precipitate and the supernatant obtained by centrifugation at 4000 rpm emitted strong blue fluorescent light.

In the first and fourth steps, an aqueous sodium hydroxide solution containing zinc ions and thioglycolic acid was used in place of aqueous ammonia. The thus obtained precipitate and supernatant emitted stronger fluorescent light than those obtained by using aqueous ammonia.

When an aqueous sodium hydroxide solution containing zinc ions and thioglycolic acid was used in the first and fourth steps, the mean particle size of the (zinc selenide/cadmium selenide alloy)-(zinc sulfide/cadmium sulfide alloy) core-shell nanoparticle-dispersed small glass particles contained in the supernatant was measured using a light scattering particle size analyzer, and found to be about 30 nm. The fluorescence spectrum of the blue fluorescence-emitting transparent supernatant was not so different from that of the semiconductor nanoparticle-dispersed aqueous solution used as the starting material. The emission peak wavelength was 449 nm, and the fluorescence quantum yield was estimated to be 30%.

Further, the procedures were performed in the same manner as in Example 3. A strong blue fluorescence-emitting powder of (zinc selenide/cadmium selenide alloy)-(zinc sulfide/cadmium sulfide alloy) core-shell nanoparticle-dispersed small glass particles was thereby obtained.

Example 5

II-VI semiconductor zinc selenide-zinc telluride alloy nanoparticles were produced according to the method described in Li, Murase, Chemistry Letters, vol. 34, page 92 (2005). More specifically, while vigorously stirring an aqueous solution of zinc perchlorate adjusted to pH 6.5, hydrogen selenide gas and hydrogen telluride gas were allowed to react in the presence of thioglycolic acid (HOOCCH$_2$SH) as a surfactant under an argon gas atmosphere. Clusters containing zinc selenide and zinc telluride were thereby produced in the aqueous solution, and this aqueous solution was refluxed under atmospheric pressure for several tens of hours to produce zinc selenide-zinc telluride alloy nanoparticles having a mean particle size of 3 nm and emitting bluish violet light under UV excitation.

The zinc selenide/zinc telluride alloy nanoparticles were dispersed in an aqueous solution containing zinc ions and thioglycolic acid, then adjusted to pH 10 to 11 and subjected to UV irradiation to conduct post-processing. A core-shell nanoparticle comprising a zinc selenide-zinc telluride alloy particle as the core whose surface was coated with a thin zinc sulfide shell layer was thereby prepared. This core-shell nanoparticle emitted bluish violet light.

Using the thus obtained semiconductor nanoparticles, the first to third steps and the fourth step (post-processing step) were performed in the same manner as in Example 4 except that an aqueous sodium hydroxide solution containing zinc ions and thioglycolic acid was used. As a result, a solution of zinc (selenide/zinc telluride alloy)-zinc sulfide core-shell nanoparticle-dispersed small glass particles was obtained. Both the precipitate and the supernatant obtained by centrifuging this solution at 4000 rpm emitted strong blue fluorescent light (emission wavelength: 430 mm).

Further, the procedures were performed in the same manner as in Example 3. A strong bluish violet fluorescence-emitting powder of (zinc selenide/zinc telluride alloy)-zinc sulfide core-shell nanoparticle-dispersed small glass particles was thereby obtained.

Example 6

Using red light-emitting semiconductor cadmium telluride nanoparticles with a mean particle size of 4 nm produced in the same manner as in Example 1, the first to third steps were performed in the same manner as in Example 1. In the subsequent fourth step (post-processing step), $1.0 \times 10^{-3}$ mol of TEOS and aqueous ammonia were added to the solution and stirred for 4 hours and then ultrasonic vibration was applied at room temperature for 30 minutes.

In order that not only OH groups but also amino groups effectively used to bond the small glass particles to biomolecules were present on the outermost surfaces of the thus obtained cadmium telluride nanoparticle-dispersed small glass particles, $3.4 \times 10^{-4}$ mol of 3-aminopropyltrimethoxysilane (APS) and aqueous ammonia were added to the solution of the cadmium telluride nanoparticle-dispersed small glass particles, and stirred for 1 hour. Ultrasonic vibration was then applied at room temperature for 30 minutes.

The obtained solution was centrifuged at 4000 rpm to separate a brown precipitate and a transparent supernatant. Both the precipitate and the supernatant emitted red fluorescent light under UV excitation. The shape (spherical) of the thus obtained cadmium telluride nanoparticle-dispersed small glass particles, particle size (diameter) thereof, the fluorescent wavelength, and the fluorescence quantum yield were the same as in Example 1.

The particle size of the small glass particles after the addition of APS was larger than that before the addition. Thus the results show that APS added in the fourth step (post-processing step) is hydrolyzed to form a glass layer on the outermost surface of the cadmium telluride nanoparticle-dispersed small glass particles, and OH and amino groups were both present on the outermost surfaces of the final dispersed cadmium telluride nanoparticle-dispersed small glass particles.

When a green light-emitting cadmium telluride nanoparticle obtained in the same manner as in Example 2 was used in the first to fourth steps, green-emitting nanoparticle-dispersed small glass particles having both the —OH and amino groups on the outermost surface layer thereof were obtained. When bluish violet to blue light-emitting core-shell nanoparticles obtained in the same manner as in Examples 3, 4 and 5 were used in the first to fourth steps, bluish violet to blue light-emitting small glass particles incorporating zinc selenide-zinc sulfide core-shell nanoparticles, (zinc selenide/cadmium selenide alloy)-(zinc sulfide/cadmium sulfide alloy) core-shell nanoparticles, and (zinc selenide/zinc telluride alloy)-zinc sulfide core-shell nanoparticles therein, and having both the —OH and amino groups on the outermost surface layer thereof were obtained.

When $1.7 \times 10^{-4}$ mol of 3-mercaptopropyltrimethoxysilane (MPS) was used in place of $1.7 \times 10^{-4}$ mol of 3-aminopropyltrimethoxysilane (APS) in the fourth step, red, green, and bluish violet to blue light-emitting cadmium telluride nanoparticle-dispersed small glass particles and zinc selenide-zinc sulfide core-shell nanoparticle-dispersed small glass particles having both the —OH and thiol groups on the outermost surface layer were obtained.

Example 7

Because the nanoparticle-dispersed small glass particles produced by the method of the invention emits light with a very high brightness, light emission from each respective glass particle can be individually detected to obtain a spectrum.

First, the green light-emitting cadmium telluride nanoparticle (diameter: about 3 nm)-dispersed aqueous solution obtained in Example 2 was added to the red light-emitting cadmium telluride nanoparticle (diameter: about 4 nm)-dispersed aqueous solution obtained in the first step of Example 1 almost in the same amounts. Using the thus obtained aqueous cadmium telluride nanoparticle-dispersed solution mixture, nanoparticle-dispersed small glass particles were prepared in the same manner as in Example 1. Each of the thus obtained small glass particles incorporated both the red-emitting and green-emitting nanoparticles.

Small glass particles with a diameter of about 30 nm were obtained from the resulting supernatant, then diluted with water, and added dropwise onto a glass plate of non-fluorescent quartz. The resulting plate was dried in a desiccator to prepare a glass plate sample comprising small glass particles dispersed on the surface of the non-fluorescent quartz glass plate in such a concentration that about 10 nanoparticles were present per 10 μm×10 μm of the plate. In the process, care was particularly taken not to cause the aggregation of small glass particles.

As described in a publication (Murase, Chemical Physics Letters, vol. 368, page 76, 2003), this sample was irradiated with an argon laser beam of a short wavelength (488 nm) condensed by a ×40 objective lens, and a spectrum of the fluorescent light emitted therefrom was obtained using a CCD spectrometer system.

In the observation, while scanning the glass plate at the position irradiated with an argon laser using an X-, Y-micrometer, fluorescence was detected to find small glass particles.

As a result, substantially only red light emissions were detected from the small glass particles in the first position (position 1). The results show that the glass particles contained many large nanoparticles (about 4 nm in diameter).

The small glass particles in another position (position 2) emitted remarkably strong blue light. The results show that the small glass particles contained many small nanoparticles (about 3 nm in diameter).

By further scanning, both red light emissions and green light emissions were observed from the small glass particles in another position (position 3). The results show that the glass particles incorporated both large and small nanoparticles.

By obtaining fluorescence spectra using such a device, the glass particles in each respective position (positions 1 to 3) were identified from the spectra.

Figure 1:
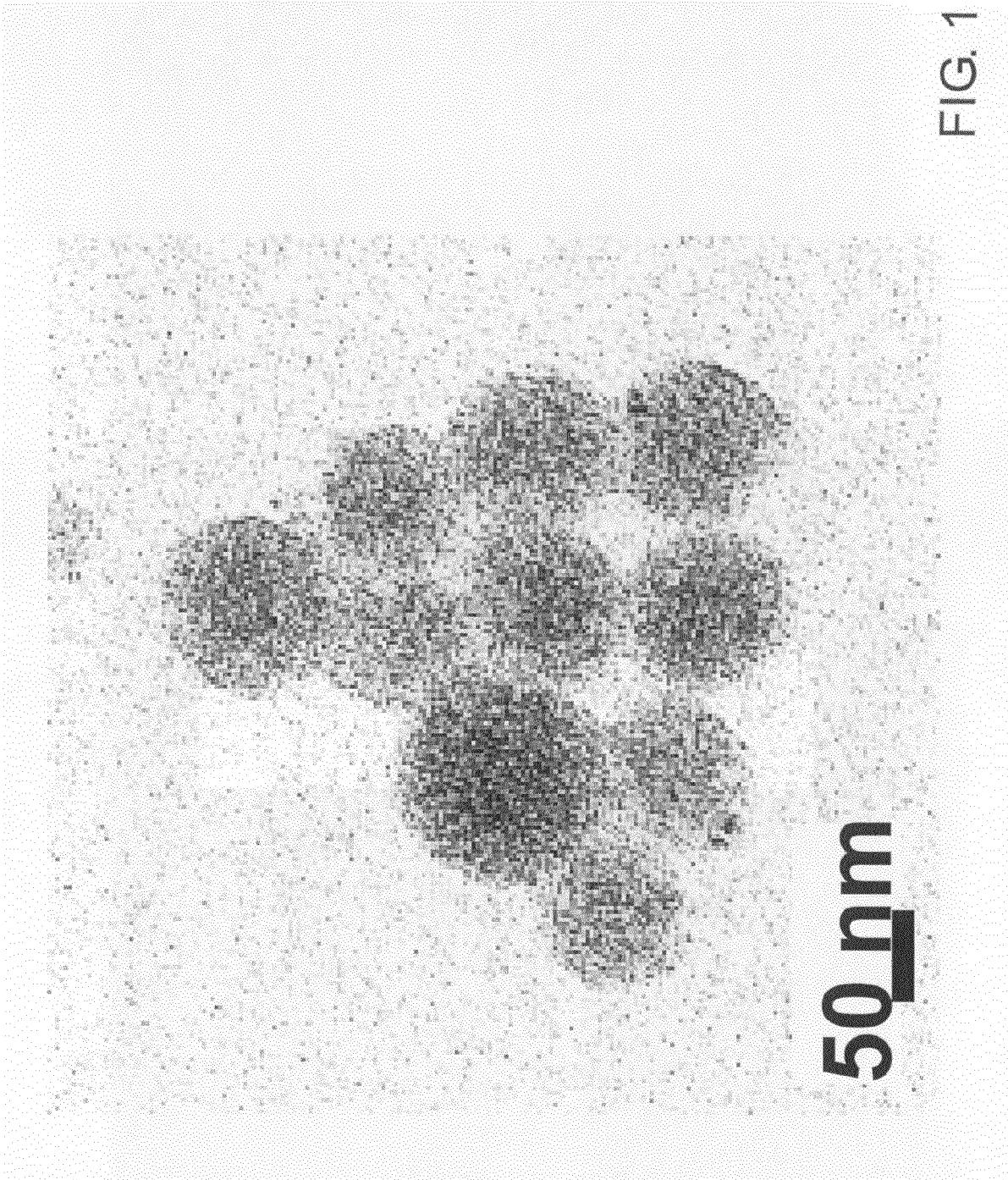
FIG. 1 shows a TEM photograph of cadmium telluride nanoparticle-dispersed small glass particles contained in the supernatant obtained by centrifugation after the fourth step.
Figure 2:
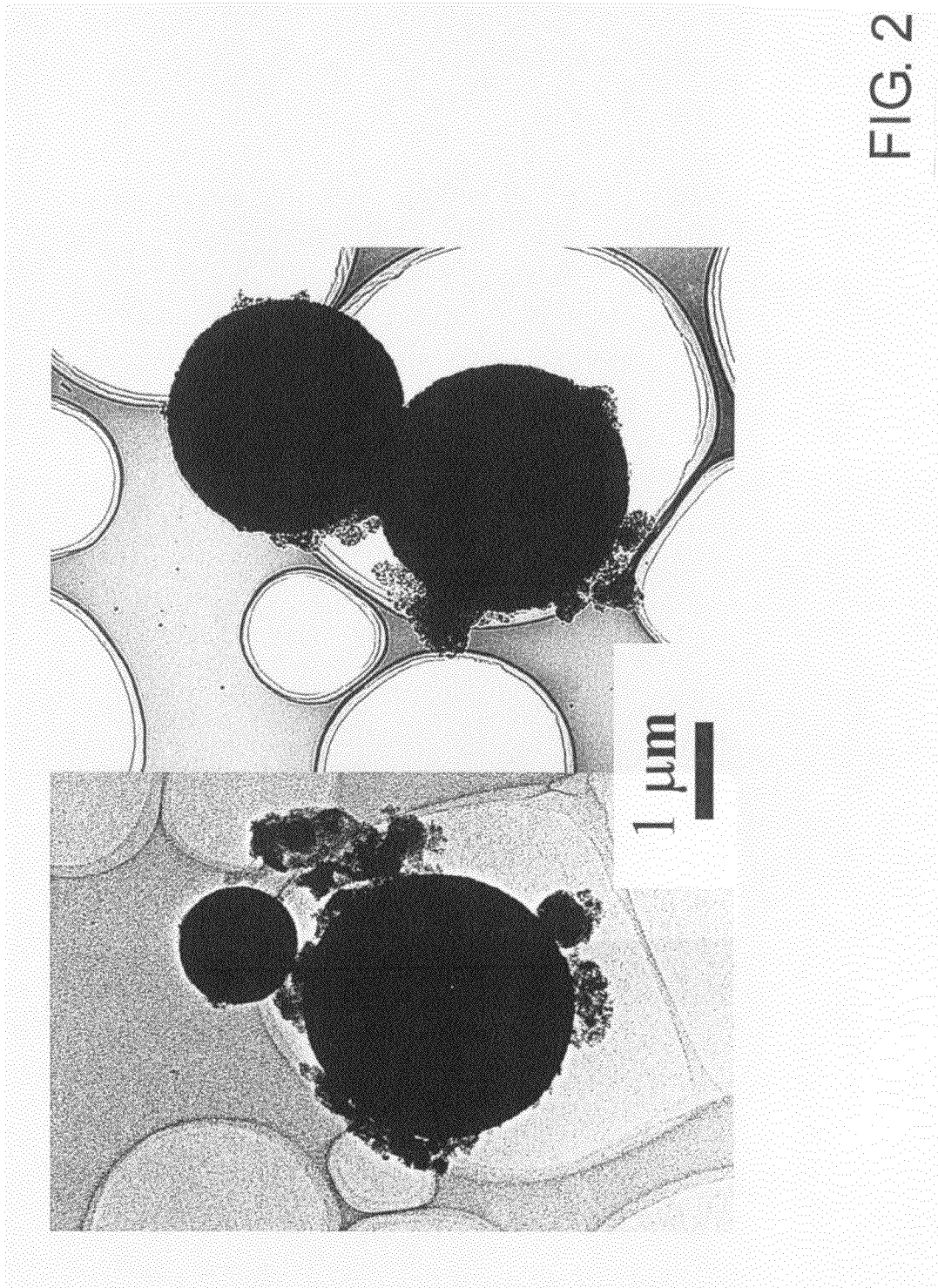
FIG. 2 shows a TEM photograph of cadmium telluride nanoparticle-dispersed small glass particles contained in the precipitate obtained by centrifugation after the fourth step.
Figure 3:
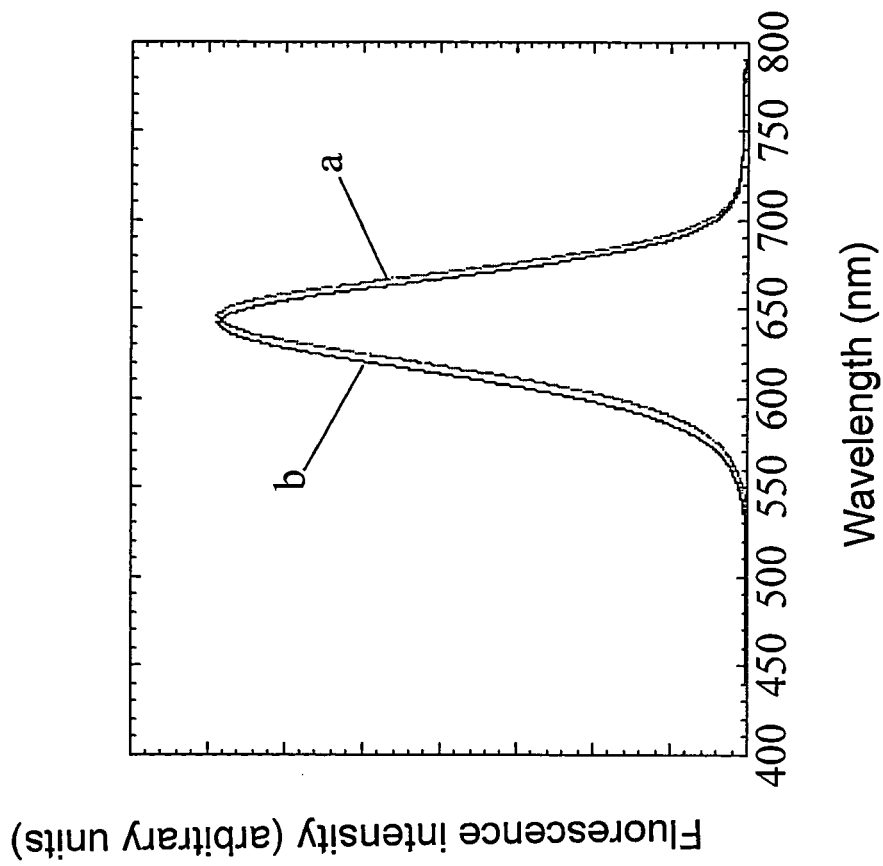
FIG. 3 shows a red fluorescence spectrum (a) of the cadmium telluride nanoparticle-dispersed aqueous solution used as the starting material, and a red fluorescence spectrum (b) of the solution of the cadmium telluride nanoparticle-dispersed small glass particles obtained as the supernatant.
Figure 4:
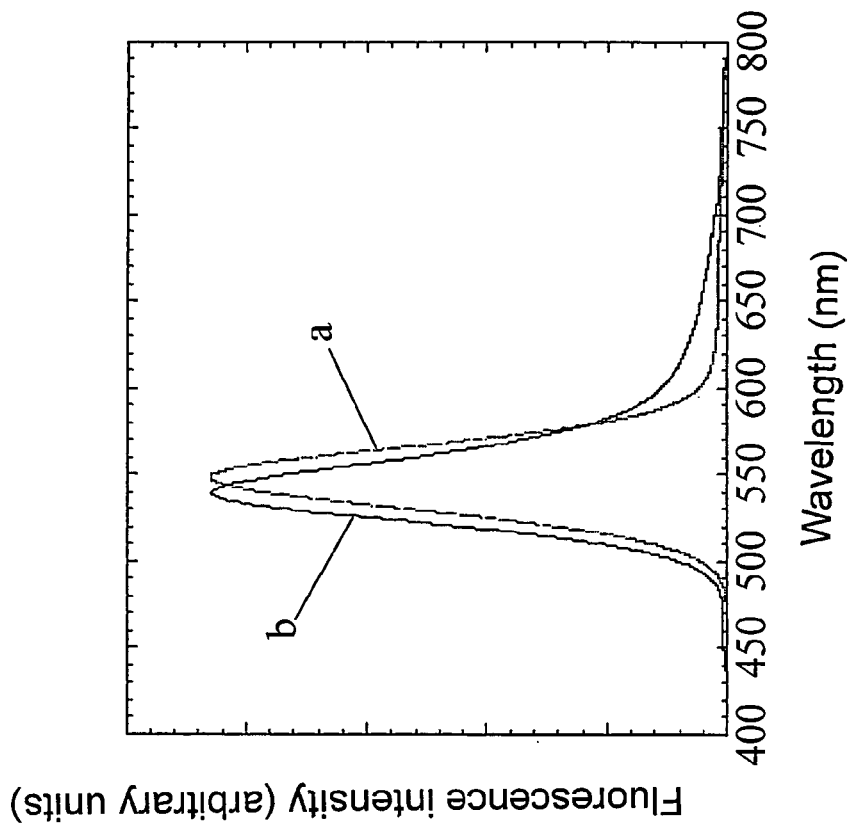
FIG. 4 shows a green fluorescence spectrum (a) of the cadmium telluride nanoparticle-dispersed aqueous solution used as the starting material, and a green fluorescence spectrum (b) of the solution of the cadmium telluride nanoparticle-dispersed small glass particles obtained as the supernatant.
Figure 5:
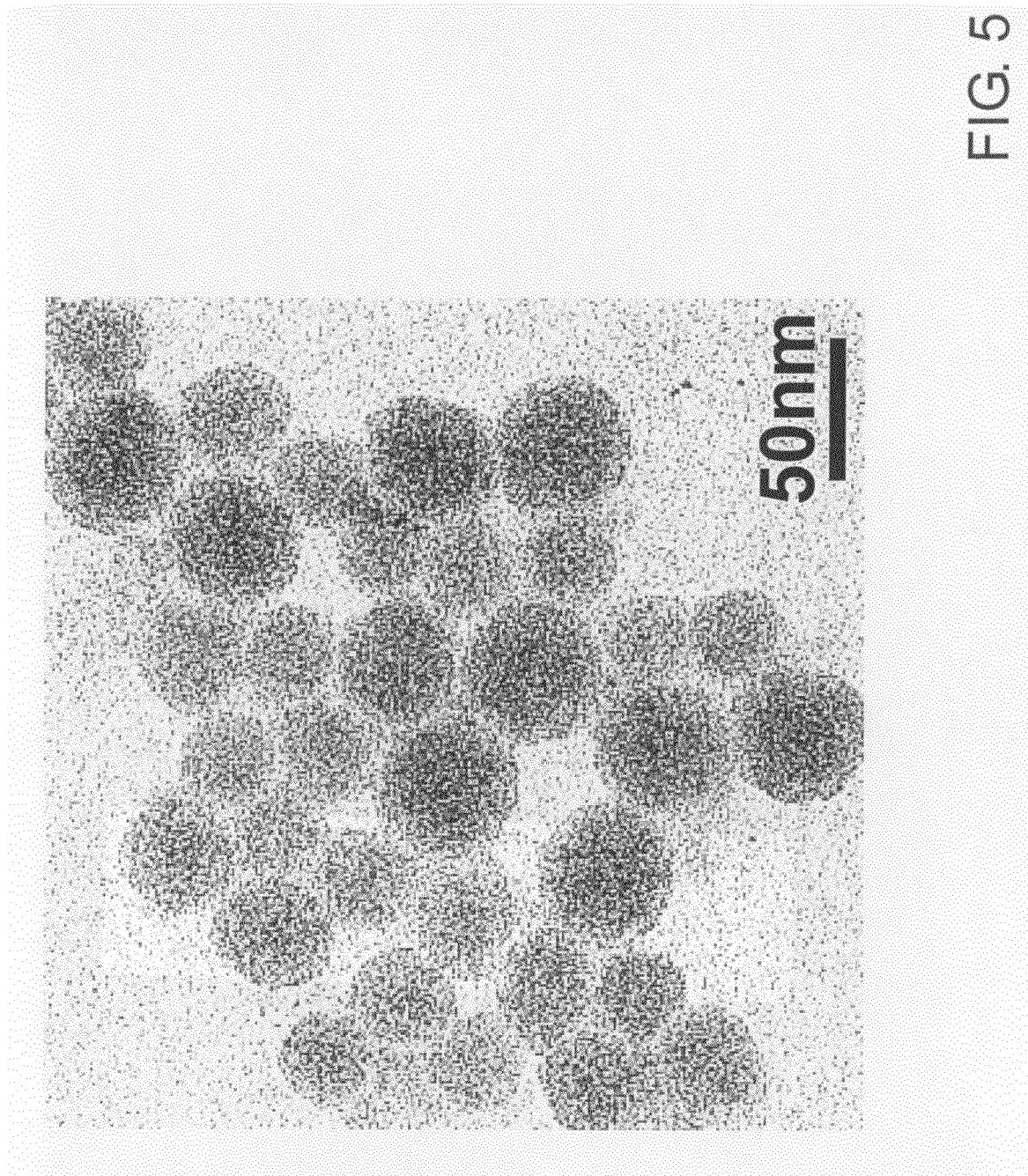
FIG. 5 shows a TEM photograph of zinc selenide-zinc sulfide core-shell nanoparticle-dispersed small glass particles contained in the supernatant obtained by centrifugation after the fourth step.
Figure 6:
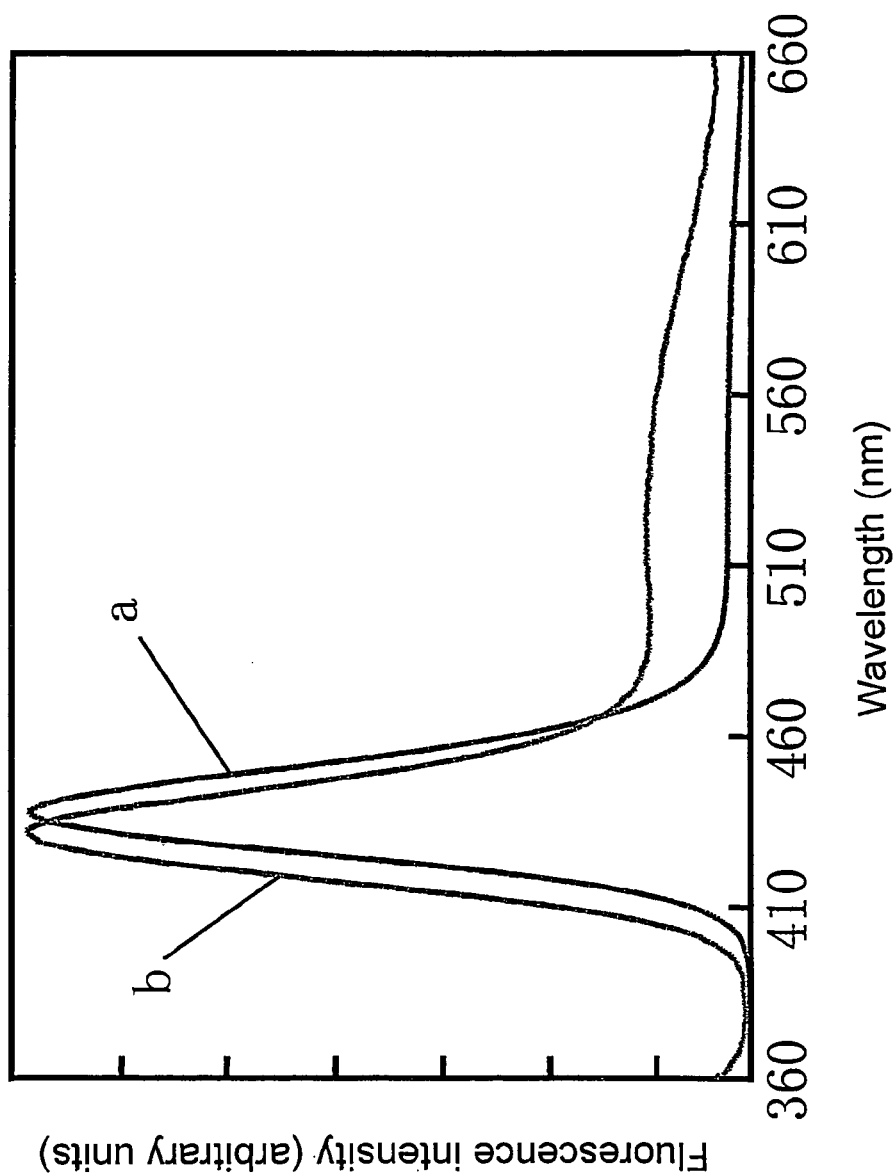
FIG. 6 shows a bluish violet fluorescence spectrum (a) of zinc selenide-zinc sulfide core-shell nanoparticle-dispersed aqueous solution used as the starting material, and a bluish violet fluorescence spectrum (b) of the solution of the zinc selenide-zinc sulfide core-shell nanoparticle-dispersed small glass particles.

The invention claimed is:

1. Semiconductor-nanoparticle-dispersed small glass particles comprising small silica glass particles comprising a hydrolyzed alkoxide and having a mean particle size of not less than 10 nanometers and not more than 5 micrometers; and semiconductor nanoparticles dispersed in the small silica glass particles in a concentration of not less than $2\times10^{-5}$ mol/l and not more than $4\times10^{-3}$ mol/l, the semiconductor-nanoparticle-dispersed small glass particles emitting fluorescent light with a fluorescence quantum yield (quantum efficiency) of 35% or more, when dispersed in a solution, wherein the mean particle size of the semiconductor particles is 2 nm or more, and wherein the semiconductor-nanoparticle-dispersed small glass particles contain more than one semiconductor nanoparticle per small silica glass particle on the average.

2. Semiconductor-nanoparticle-dispersed small glass particles comprising small silica glass particles comprising a hydrolyzed alkoxide and having a mean particle size of not less than 10 nanometers and not more than 5 micrometers; and semiconductor nanoparticles dispersed in the small silica glass particles in a concentration of not less than $2\times10^{-5}$ mol/l and not more than $4\times10^{-3}$ mol/l, the semiconductor-nanoparticle-dispersed small glass particles emitting fluorescent light with a fluorescence quantum yield (quantum efficiency) of 35% or more, when dispersed in a solution, which contain more than one semiconductor nanoparticle per small silica glass particle on the average.

3. Semiconductor-nanoparticle-dispersed small glass particles according to claim 2 which emit fluorescent light with a fluorescence quantum yield (quantum efficiency) of 60% or more, when dispersed in a solution.

4. Semiconductor-nanoparticle-dispersed small glass particles according to claim 3 wherein the semiconductor nanoparticle is at least one member selected from the group consisting of cadmium sulfide, zinc selenide, cadmium selenide, zinc telluride, cadmium telluride, zinc sulfide, and lead sulfide.

5. Semiconductor-nanoparticle-dispersed small glass particles according to claim 4 having at least one functional group selected from the group consisting of amino, thiol, and carboxyl groups on the surfaces of the small glass particles.

6. A fluorescent material containing the semiconductor-nanoparticle-dispersed small glass particles of claim 1.

7. Semiconductor-nanoparticle-dispersed small glass particles according to claim 1 which emit fluorescent light with a fluorescence quantum yield (quantum efficiency) of 60% or more, when dispersed in a solution.

8. Semiconductor-nanoparticle-dispersed small glass particles according to claim 7 wherein the semiconductor nanoparticle is at least one member selected from the group consisting of cadmium sulfide, zinc selenide, cadmium selenide, zinc telluride, cadmium telluride, zinc sulfide, and lead sulfide.

9. Semiconductor-nanoparticle-dispersed small glass particles according to claim 8 having at least one functional group selected from the group consisting of amino, thiol, and carboxyl groups on the surfaces of the small glass particles.

10. Semiconductor-nanoparticle-dispersed small glass particles according to claim 1 wherein the semiconductor nanoparticle is at least one member selected from the group consisting of cadmium sulfide, zinc selenide, cadmium selenide, zinc telluride, cadmium telluride, zinc sulfide, and lead sulfide.

11. Semiconductor-nanoparticle-dispersed small glass particles according to claim 10 having at least one functional group selected from the group consisting of amino, thiol, and carboxyl groups on the surfaces of the small glass particles.

12. Semiconductor-nanoparticle-dispersed small glass particles according to claim 1 having at least one functional group selected from the group consisting of amino, thiol, and carboxyl groups on the surfaces of the small glass particles.

* * * * *